(12) United States Patent
Mousa et al.

(10) Patent No.: US 12,274,693 B2
(45) Date of Patent: *Apr. 15, 2025

(54) ANTI-PROPROTEIN CONVERTASE SUBTILISIN KEXIN TYPE 9 (ANTI-PCSK9) NANO-FORMULATION OF COMPOUNDS AND METHODS OF USING THE SAME

(71) Applicant: SHIFA BIOMEDICAL CORPORATION, Malvern, PA (US)

(72) Inventors: Shaker A. Mousa, Wynantskill, NY (US); Nabil A. Elshourbagy, West Chester, PA (US); Harold V. Meyers, Weston, MA (US); Sherin Salaheldin Abdel-Meguid, Exton, PA (US)

(73) Assignee: SHIFA BIOMEDICAL CORPORATION, Malvern, PA (US)

( * ) Notice: Subject to any disclaimer, the term of this patent is extended or adjusted under 35 U.S.C. 154(b) by 863 days.

This patent is subject to a terminal disclaimer.

(21) Appl. No.: 17/276,543

(22) PCT Filed: Nov. 5, 2019

(86) PCT No.: PCT/US2019/059777
§ 371 (c)(1),
(2) Date: Mar. 16, 2021

(87) PCT Pub. No.: WO2020/097016
PCT Pub. Date: May 14, 2020

(65) Prior Publication Data
US 2022/0031665 A1 Feb. 3, 2022

Related U.S. Application Data

(60) Provisional application No. 62/755,709, filed on Nov. 5, 2018.

(51) Int. Cl.
*A61K 31/422* (2006.01)
*A61K 9/51* (2006.01)
*A61K 45/06* (2006.01)
*A61K 47/55* (2017.01)

(52) U.S. Cl.
CPC .......... *A61K 31/422* (2013.01); *A61K 9/5138* (2013.01); *A61K 9/5153* (2013.01); *A61K 9/5161* (2013.01); *A61K 45/06* (2013.01); *A61K 47/55* (2017.08)

(58) Field of Classification Search
None
See application file for complete search history.

(56) References Cited

U.S. PATENT DOCUMENTS 9,040,727 B2 * 5/2015 Li .................... C07C 237/48
549/462
9,682,085 B2   6/2017 Abdel-Meguid et al.
9,956,291 B2   5/2018 Mousa
10,899,748 B2 * 1/2021 Abdel-Meguid .... C07D 413/12
10,947,220 B2 * 3/2021 Abdel-Meguid .... C07D 405/12
2014/0017329 A1 * 1/2014 Mousa ............... A61K 47/6939
424/502
2016/0303054 A1  10/2016 Yacoub et al.

FOREIGN PATENT DOCUMENTS

WO  2014/150326 A1  9/2014
WO  2017/222953 A1  12/2017

OTHER PUBLICATIONS

CAS STNext Registry File. Registry No. 2170496-21-4. Retrieved from the internet on Feb. 7, 2024, https://www.stn.org/stn/#/. Published Jan. 17, 2018. (Year: 2018).*
Wang et al. Aggregation of Hydroxypropyl Methylcellulose Acetate Succinate under Its Dissolving pH and the Impact on Drug Supersaturation. Molecular Pharmaceutics 2018 15 (10), 4643-4653 (Year: 2018).*
Kuckzkur et al. Polyvinylpyrrolidone (PVP) in nanoparticle synthesis. Dalton Transactions. Published 2015. (Year: 2015).*
Cheng, Y., et al., "Alginic Acid Nanoparticles Prepared through Counterion Complexation Method as a Drug Delivery System" ACS Appl. Mater. Interfaces (2012) 4:5325-5332.
Addisu, K.D., et al., "Mixed Lanthanide Oxide Nanoparticles Coated with AlginatePolydopamine as Multifunctional Nanovehicles for Dual Modality: Targeted Imaging and Chemotherapy" ACS Biomater. Sci. Eng. (2019) 5:5453-5469.
Patra, A., et al., "Nanodelivery and anticancer effect of a limonoid, nimbolide, in breast and pancreatic cancer cells" International Journal of Nanomedicine (2019) 14:8095-8104.
Gupta, N., et al., "Advancement in nanotechnology-based approaches for the treatment and diagnosis of hypercholesterolemia" Artificial Cells, Nanomedicine, and Biotechnology (2018) 46(S1):S188-S197.
Bobo, D., et al., "Nanoparticle-Based Medicines: A Review of FDA-Approved Materials and Clinical Trials to Date" Pharm. Res, (2016) 33(10):2373-87.
Caster, J.M., et al., "Investigational nanomedicines in 2016: a review of nanotherapeutics currently undergoing clinical trials" Wiley Interdiscip Rev Nanomed Nanobiotechnol (2016) 9:e1416.
Havel, H.A., et al., "Where Are the Nanodrugs? An Industry Perspective on Development of Drug Products Containing Nanomaterials" AAPS J. (2016) 18:1351-3.
Havel, H., et al., "Nanomedicines: From Bench to Bedside and Beyond" AAPS J. (2016) 18:1373-8.
Rohilla, et al., "Herbal and polymeric approaches for liver-targeting drug delivery: novel strategies and their significance" Drug Deliv. (2016) 23(5):1645-1661.

* cited by examiner

*Primary Examiner* — James H Alstrum-Acevedo
*Assistant Examiner* — Lauren Wells
(74) *Attorney, Agent, or Firm* — Robert C. Netter, Jr.; Dann, Dorfman, Herrell & Skillman

(57) ABSTRACT

Disclosed are Nanoformulated compounds that modulate the physiological action of the proprotein convertase subtilisin kexin type 9 (PCSK9), as well as therapeutic methods for use of such compounds to reduce LDL- and related cholesterol levels and/or for the treatment and/or prevention of cardiovascular disease (CVD), including treatment of hypercholesterolemia.

30 Claims, 23 Drawing Sheets
Specification includes a Sequence Listing.

| | | Size (d.nm): | % Intensity: | St Dev (d.nm): |
|---|---|---|---|---|
| Z-Average (d.nm): 153.7 | Peak 1: | 207.0 | 98.2 | 124.7 |
| PdI: 0.290 | Peak 2: | 5083 | 1.5 | 562.5 |
| Intercept: 0.964 | Peak 3: | 13.42 | 0.3 | 2.538 |
| Result quality: Good | | | | |

Preparation of Nano SBC-115,418 for Efficacy & Safety Studies

Stability Study

| Date | SBC-115,418 Concentration (mg/ml) | Average Size (nm) | Zeta Potential (mV) |
|---|---|---|---|
| Day 1 | 40.8 | 107 | -287 |
| Week 1 | 41.6 | 105 | -288 |
| Week 2 | 41.2 | 102 | -289 |
| Week 3 | 41.6 | 115 | -29 |

SEQUENCE LISTING

```
<160> NUMBER OF SEQ ID NOS: 1

<210> SEQ ID NO 1
<211> LENGTH: 692
<212> TYPE: PRT
<213> ORGANISM: Homo sapiens

<400> SEQUENCE: 1

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240
```

```
Val Ala Lys Gly Ala Ser Met Arg Ser Leu Arg Val Leu Asn Cys Gln
            245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
            290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
            370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
            450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
            530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
            595                 600                 605

Lys Val Lys Glu His Gly Ile Pro Ala Pro Gln Glu Gln Val Thr Val
            610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655
```

```
Arg Ser Arg Asp Val Ser Thr Thr Gly Ser Thr Ser Glu Gly Ala Val
            660                 665                 670
Thr Ala Val Ala Ile Cys Cys Arg Ser Arg His Leu Ala Gln Ala Ser
            675                 680                 685
Gln Glu Leu Gln
        690
```

ANTI-PROPROTEIN CONVERTASE SUBTILISIN KEXIN TYPE 9 (ANTI-PCSK9) NANO-FORMULATION OF COMPOUNDS AND METHODS OF USING THE SAME

This application is a § 371 application of PCT/US2019/059777, filed Nov. 5, 2019, which in turn claims priority under 35 U.S.C. § 119(e) to U.S. Provisional Patent Application No. 62/755,709, filed Nov. 5, 2018. The foregoing applications are incorporated by reference herein.

STATEMENT REGARDING FEDERAL SPONSORED RESEARCH OR DEVELOPMENT

This invention was made with government support under SBIR Grant No. HL137449 awarded by the National Heart, Lung and Blood Institute (NHLBI). The government has certain rights in the invention.

FIELD OF INVENTION

The present invention relates to the Nano-formulation of compounds that modulate the physiological action of the proprotein convertase subtilisin kexin type 9 (PCSK9), including its interaction with the low-density lipoprotein receptor (LDLR). In certain embodiments, the invention relates to compositions and associated methods for hepatic-targeted delivery of PCSK9 inhibitors or antagonists such as SBC-115,418 or its analogues (see, e.g., WO 2017/222953) to the liver of a subject. In certain embodiments, compositions are provided which include hydrophobic nanoparticles, a liver-targeting moiety attached or linked (e.g., covalently) to the exterior of each nanoparticle (see, e.g., U.S. Pat. No. 9,682,085), and at least one PCSK9 inhibitor or antagonist (e.g., SBC-115,418) encapsulated within each nanoparticle. The nanoparticles may include chitosan hybrid nanoparticles, amine modified poly-(lactic-co-glycolic acid) (PLGA) nanoparticles, solid lipid nanoparticles (SLNs), and/or combinations thereof. Examples of liver-targeting moieties include Glycyrrhetinic acid (GA), Lactobionic acid (LA), Alginic acid, and/or combinations thereof. The small molecule modulators of PCSK9 function can be used therapeutically to lower LDL-cholesterol levels in blood and can be used in the prevention and/or treatment of cholesterol, lipid, and lipoprotein metabolism disorders, including hypercholesterolemia, familial hypercholesterolemia, atherogenic dyslipidemia, atherosclerosis, and more generally, cardiovascular disease (CVD), diabetes, and for obese subjects with high cardiovascular risk.

BACKGROUND OF INVENTION

Cardiovascular diseases (CVDs) are the leading cause of death, with atherosclerosis being the leading cause of cardiovascular diseases. Atherosclerosis is a disease of the arteries and is responsible for coronary heart disease associated with many deaths in industrialized countries. Several risk factors for coronary heart disease have now been identified including, without limitation: dyslipidemia, hypertension, diabetes, smoking, poor diet, inactivity and stress. Dyslipidemia is elevation of plasma cholesterol (hypercholesterolemia) and/or triglycerides (TGs) or a low high-density lipoprotein (HDL) level that contributes to the development of atherosclerosis, which is a metabolic disorder proven to contribute to cardiovascular disease. In the blood, cholesterol is transported in lipoprotein particles, where the low-density lipoprotein (LDL) cholesterol (LDL-C) is considered "bad" cholesterol, while HDL-cholesterol (HDL-C) is known as "good" cholesterol. Lipid and lipoprotein abnormalities are extremely common in the general population and are regarded as a highly modifiable risk factor for cardiovascular disease, due to the influence of cholesterol on atherosclerosis. There is a significant unmet need with respect to CVD with 60-70% of cardiovascular events, heart attacks and strokes occurring despite the treatment with statins (the current standard of care in atherosclerosis). Moreover, new guidelines suggest that even lower LDL levels should be achieved in order to protect high-risk patients from premature CVD (1).

The establishment of a link between PCSK9 and cholesterol metabolism was rapidly followed by the discovery that selected mutations in the PCSK9 gene caused autosomal dominant hypercholesterolemia (2), suggesting that the mutations confer a gain-of-function (3) by increasing the normal activity of PCSK9. This was supported by the experiment in which wild type and mutant PCSK9 (S127R and F216L) were expressed at high levels in the livers of mice and it was found that hepatic LDLR protein levels fell dramatically in mice receiving either the wild type or mutant PCSK9 (4, 5). No associated reductions in LDLR mRNA levels were observed, indicating that overexpression of PCSK9, whether mutant or wild type reduces LDLRs through a post-transcriptional mechanism.

Given that gain-of-function mutations in PCSK9 cause hypercholesterolemia, it was reasonable to ask if loss-of-function mutations would have the opposite effect and result in hypocholesterolemia. Three loss-of-function mutations in PCSK9 (Y142X, L253F, and C679X) were identified in African-Americans (6). These mutations reduce LDL-C levels by 28% and were shown to decrease the frequency of coronary heart disease (defined as myocardial infarction, coronary death or coronary revascularization) by 88%. Rashid et al. (7) studied the mechanism of loss-of-function mutations in mice where PCSK9 was inactivated. They reported that these knockout mice showed increased hepatic LDLR protein (but not mRNA), increased clearance of circulating lipoproteins and reduced plasma cholesterol levels. Structure-function relationship analysis of the naturally occurring mutations in PCSK9 has also provided insights into the mechanism of action of PCSK9. Interestingly, mutations in PCSK9 that were found to be associated with the greatest reductions in LDL-C plasma levels are those that prevent the secretion of mature PCSK9 by disrupting its synthesis (Y142X), autocatalytic processing (L253F), or folding (C679X) (8). The Y142X mutation produces no detectable protein because it occurs early in the transcript and is predicted to initiate nonsense-mediated mRNA decay. Mutations in the catalytic domain (L253F) interfere with the autocatalytic cleavage of the protein. In cells expressing the PCSK9-253F, the amount of mature protein was reduced compared to that in cells expressing PCSK9-WT, suggesting that the mutation inhibits autocatalytic cleavage. The L253F mutation is near the catalytic triad (PCSK9 is a serine protease), therefore it might disrupt the active site (8). Inasmuch as autocatalytic cleavage of PCSK9 is required for export of the protein out of the endoplasmic reticulum (ER), the L253F mutation delays transport of PCSK9 from the ER to the cell surface. The nonsense mutation (C679X) in PCSK9, which truncates the protein by 14 amino acids, did not interfere with protein processing, but the mature protein accumulates in the cells and none is secreted, suggesting that the protein is cleaved normally but is misfolded and is retained in the ER (8, 9).

The mechanism by which PCSK9 causes the degradation of the LDLR has not been fully elucidated. However, it is clear that the protease activity of PCSK9 is not required for LDLR degradation (10, 11). Li et al. (10) have co-expressed the pro-domain and the catalytic domain and showed that the secreted PCSK9 was catalytically inactive, yet it is functionally equivalent to the wild-type protein in lowering cellular LDL uptake and LDLR levels. McNutt et al. (11) also reported similar studies. Furthermore, Zhang et al. (12) has mapped PCSK9 binding to the EGF-A repeat of the LDLR and showed that such binding decreases the receptor recycling and increases its degradation. They also reported that binding to EGF-A domain was calcium-dependent and increased dramatically with reduction in pH from 7 to 5.2. Kwon et al. (13) determined the crystal structure of PCSK9 in complex with the LDLR-EGF-AB (EGF-A and EGF-B). The structure shows a well-defined EGF-A domain, but the EGF-B domain is disordered and absent from their electron density map. The EGF-A domain binds to the PCSK9 catalytic domain at a site distant from the catalytic site and makes no contact with either the C-terminal domain or the pro-domain (14).

Several strategies have been proposed for targeting PCSK9 (15). Strategy 1: mRNA knockdown approaches including the use of antisense oligonucleotides or RNAi. Antisense oligonucleotides administered to mice reduced PCSK9 expression by >90% and lowered plasma cholesterol levels by 53% (16). A single intravenous injection of an RNAi delivered in lipidoid nanoparticles to cynomolgous monkeys reduced plasma PCSK9 levels by 70% and plasma LDL-C levels by 56% (17). Strategy 2: the development of small-molecule inhibitors of PCSK9 processing. Despite evidence that the catalytic activity of PCSK9 is not required for LDLR degradation (11), an intracellular inhibitor of PCSK9 catalytic activity should be effective, since autocatalytic processing of PCSK9 is required for secretion of the protein from the ER. Following its synthesis, PCSK9 undergoes an autocatalytic cleavage reaction that clips off the pro-domain, but the pro-domain remains attached to the catalytic domain (18, 19). The autocatalytic processing step is required for the secretion of PCSK9 (20), likely because the pro-domain serves as a chaperone and facilitates folding. The continued attachment of the pro-domain partially blocks the substrate-binding pocket of PCSK9 (18, 19). Strategy 3: is to prevent binding of PCSK9 to the LDLR on the cell surface with a small molecule, a peptide, or an antibody directed against PCSK9. McNutt et al. (21) demonstrated that antagonism of secreted PCSK9 increases LDLR expression in HepG2 cells. They show that an FH-associated LDLR allele (H306Y) that results in a gain-of-function mutation is due to an increase in the affinity of PCSK9 to the LDLR, which would lead to enhanced LDLR destruction, and decreased plasma LDL-C clearance. Furthermore, they were able to show that blocking the secreted PCSK9 with LDLR (H306Y) sub-fragment resulted in an increase in the level of LDLR in cultured HepG2 cells. Therefore, PCSK9 acts as a secreted factor to cause LDLR degradation, and a small molecule inhibitor that interferes with the binding of PCSK9 to the LDLR will diminish LDLR destruction and increase plasma LDL-C clearance.

Currently (22-24), there are FDA approved injectable PCSK9 monoclonal antibody antagonists on the market. These are Regeneron/Sanofi's PRALUENT (alirocumab) and Amgen's REPATHA (evolocumab), both of which are fully human anti-PCSK9 monoclonal antibodies. These monoclonal antibody approaches follow Strategy 3 using injectable antibodies instead of oral small molecules.

SUMMARY OF THE INVENTION

This invention relates to therapeutic applications of Nano-formulated small molecules, optionally hepatic-targeted, that selectively interact with and down modulate PCSK9 function. In a first embodiment, the compounds used in the practice of this invention have the general Formula I:

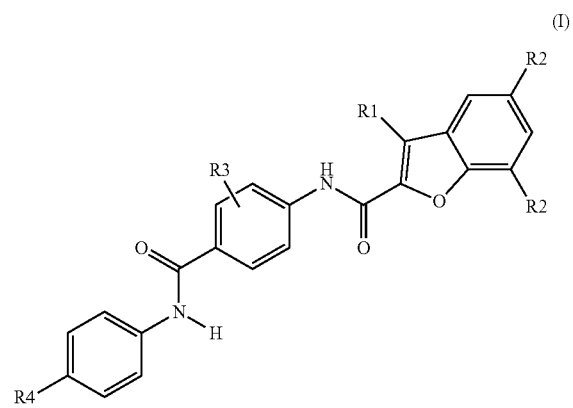

(I)

including pharmaceutically acceptable salts and stereoisomers of the compounds, wherein $R_1$ is independently selected from the group consisting of H and $CH_3$; $R_2$ and $R_3$ are independently selected from the group consisting of H, halogen, $(C_1-C_3)$-alkyl and $(C_1-C_3)$-alkoxy; and $R_4$ is independently selected from the group consisting of $CO_2R_5$, $CONR_5R_6$, aryl and heteroaryl, wherein $R_5$ and $R_6$ are independently selected from the group consisting of H and $(C_1-C_3)$-alkyl. In a particular embodiment, $R_4$ is an aryl or heteroaryl. In a particular embodiment, $R_4$ is selected from the group consisting of 2-oxazole, 2-oxazoline, 2-benzoxazole and 2-benzimidazole.

In a particular embodiment, the present invention provides for compounds of Formula II:

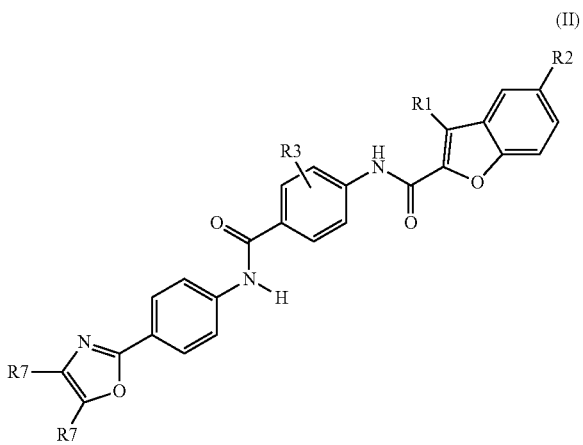

(II)

including pharmaceutically acceptable salts and stereoisomers of the compounds, wherein $R_1$ is independently selected from the group consisting of H and $CH_3$; $R_2$ is H or methoxy; $R_3$ is H or halogen; and $R_7$ is independently selected from the group consisting of H and $(C_1-C_2)$-alkyl or taken together form an optionally substituted 6-membered carbo-cycle, including aryl. In a particular embodiment, when $R_1$ is H then $R_2$ is H. In a particular embodiment, when $R_1$ is methyl then $R_2$ is methoxy. In a particular embodiment, $R_3$ is fluorine (e.g., 2-F or 3-F). In a particular embodiment, the oxazole is replaced with imidazole (i.e., the oxygen is replaced with a nitrogen).

The present invention further provides a composition for hepatic-targeted delivery of a PCSK9 antagonist to a liver of a subject. In a particular embodiment, the composition comprises nanoparticles (e.g., hydrophobic nanoparticles), at least one liver targeting moiety attached to the exterior of each nanoparticle (e.g., covalently bonded), and at least one PCSK9 antagonist (e.g., a compound of Formula I or II) encapsulated within each nanoparticle. In a particular embodiment, the hydrophobic nanoparticles are selected from the group consisting of chitosan hybrid nanoparticles, amine-modified poly-(lactic-co-glycolic acid) (PLGA) nanoparticles, solid lipid nanoparticles, and/or combinations thereof. In a particular embodiment, the liver targeting moiety is selected from the group consisting of Glycyrrhetinic acid (GA; enoxolone), Lactobionic acid (LA), Alginic acid, and/or combinations thereof.

The present invention further provides methods for targeted delivery of a PCSK9 antagonist (e.g., SBC-115,418 and analogs thereof, compounds of Formula I or II) to the liver of a subject. In a particular embodiment, the method comprises administering a composition to the subject, wherein the composition comprises nanoparticles (e.g., hydrophobic nanoparticles), at least one liver targeting moiety attached to the exterior to each nanoparticle (e.g., covalently bonded), and at least one PCSK9 antagonist (e.g., a compound of Formula I or II) encapsulated within each nanoparticle. The methods can be to treat, inhibit, and/or prevent hypercholesterolemia (e.g., familial hypercholesterolemia), dyslipidemia (e.g., atherogenic dyslipidemia), atherosclerosis, and/or cardiovascular disease (CVD) in a subject in need thereof.

In a particular embodiment, the hydrophobic nanoparticles are as described in U.S. Pat. No. 9,956,291 (incorporated herein by reference). In a particular embodiment, the hydrophobic nanoparticles are positively charged. In a particular embodiment, the hydrophobic nanoparticles have a diameter less than 1 µm, particularly 1 nm to about 500 nm, particularly 50 nm to about 300 nm. In a particular embodiment, the hydrophobic nanoparticles are chitosan hybrid nanoparticles, amine-modified poly-(lactic-co-glycolic acid) (PLGA) nanoparticles, solid lipid nanoparticles (SLNs), polyvinyl pyrrolidone (PVP) nanoparticles, hydroxypropyl methylcellulose acetate succinate (HPMC-AS) nanoparticles, or combinations thereof. In a particular embodiment, the hydrophobic nanoparticles are selected from the group consisting of chitosan hybrid nanoparticles, amine-modified poly-(lactic-co-glycolic acid) (PLGA) nanoparticles, solid lipid nanoparticles, and/or combinations thereof. In a particular embodiment, the nanoparticles comprise chitosan and poly-(lactic-co-glycolic acid) (PLGA). In a particular embodiment, the nanoparticles comprise polyvinyl pyrrolidone (PVP) and hydroxypropyl methylcellulose acetate succinate (HPMC-AS). In a particular embodiment, the nanoparticles comprise polyvinyl pyrrolidone (PVP) and chitosan. In a particular embodiment, the nanoparticles comprise DSPE-PEG and/or PLGA.

In a particular embodiment, the liver targeting moiety is selected from the group consisting of Glycyrrhetinic acid (GA), Lactobionic acid (LA), Alginic acid, and/or combinations thereof. In a particular embodiment, the liver targeting moiety is coated onto the nanoparticle. In a particular embodiment, the liver targeting moiety is conjugated with the nanoparticle. In a particular embodiment, the liver targeting moiety is attached to the nanoparticle by ionic conjugation (e.g., $COO^-$ with $NH_3^+$). In a particular embodiment, the liver targeting moiety is covalently attached to the nanoparticle.

In a particular embodiment, the PCSK9 antagonist is of Formula I or II. In a particular embodiment, the PCSK9 antagonist is selected from the group consisting of SBC-115,418, SBC-115,433, SBC-115,448, SBC-115,462 and SBC-115,477. In a particular embodiment, the PCSK9 antagonist is a compound of Formula I-V described in WO 2017/222953 (incorporated herein by reference).

In a particular embodiment, the compositions and/or methods further comprise at least one LDL-lowering substance and/or anti-dyslipidemia agent. The anti-dyslipidemia agent may be contained within (encapsulated) and/or outside the nanoparticle. In a particular embodiment, the method comprises administering the anti-dyslipidemia agent separately from the above composition. In a particular embodiment, the anti-dyslipidemia agent is selected from the group consisting of statin, ezetimibe, bempedoic acid, a thyroid hormone receptor beta agonist (TR-β agonist), and/or combinations thereof.

Entrapment efficiency (loading)=([Drug]$_f$)/([Drug]$_t$)×100, where [Drug]$_f$ is the concentration of SBC-115,418 in the nanoparticles and [Drug]$_t$ is the theoretical concentration of drug (meaning total amount of SBC-115,418 added initially). In both the nanoparticles (Formulation A & Formulation E), the entrapment was found to be more than 90%. The loading (w/w) was determined by weighing the total amount of Nano-formulations on a balance and determining the corresponding amount of SBC-115,418 with UV/VIS spectroscopy. The overall loading of SBC-115,418 in nanoparticles was found be around 4.0% w/w for Formulation A and around 6.5% w/w for Formulation E. Shown is the determination of entrapment/loading efficiency of SBC-115, 418 encapsulated in nanoparticles. Top: UV-VIS spectra used to construct the standard curve of SBC-115,418 (Inset: Concentrations of SBC-115,418 from 0.3, 0.625, 1.25, 2.5, 5 and 10 µg/mL). Middle & Bottom: Determination of entrapment efficiency by comparing OD from UV-Vis spectra of total amount SBC-115,418 (free+encapsulated) and encapsulated SBC-115,418 in Formulation A and Formulation E, respectively.

Figure 1A:
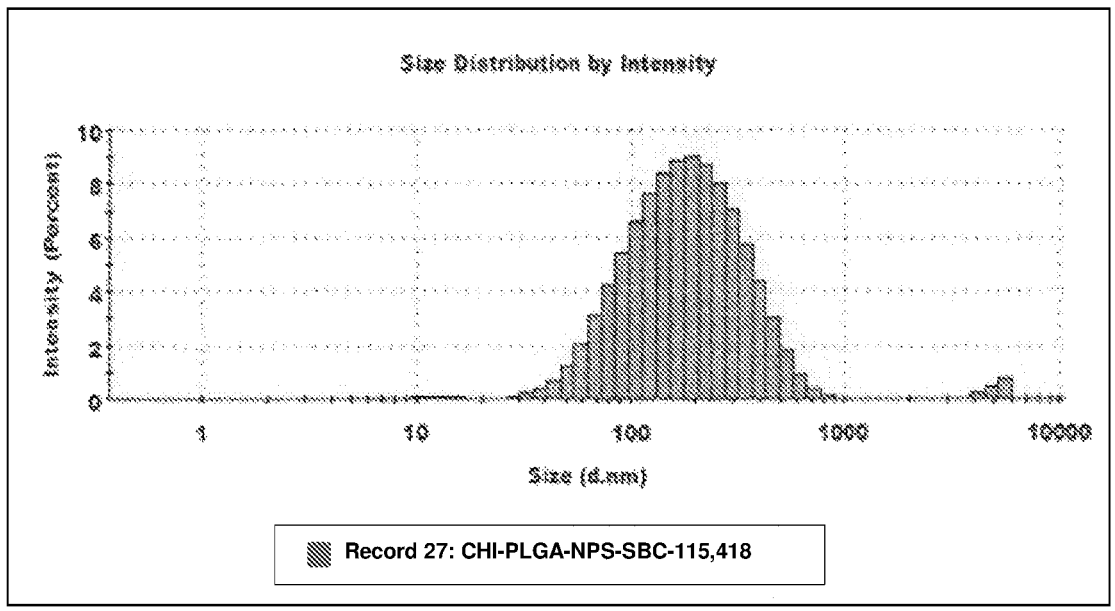
FIG. 1A provides characteristics of the synthesis of SBC-115,418 Nanoformulation A. Formulation A are Chitosan grafted poly-(lactic-co-glycolic acid) nanoparticles encapsulating SBC-115,418 (CHI-PLGA-NPS-SBC-115,418). Formulation A was prepared by the solvent diffusion method. Briefly, 20 mg of SBC-115,418 was mixed with 4 mL of PLGA solution (100 mg/ml in ethyl acetate). To this mixture, 20 mL of 2% w/v Mowiol® 4-88 (poly-(vinyl alcohol); Molecular Weight ~31,000) and 0.2% w/v chitosan solution was added and mixed thoroughly. The entire mixture was sonicated for about 90 seconds in a probe sonicator to synthesize the nanoparticles. Ethyl acetate was removed from the solution by dialysis through a 12-14 kDa cutoff dialysis membrane (for 24 hours). Finally, the nanoparticles were lyophilized using a 2% sucrose solution as a cryoprotectant. The lyophilized powder was re-dispersed and used for further studies. Shown is the size measure of SBC-115,418 nanoparticles (Formulation A) as determined by a Dynamic Light Scattering (DLS).
Figure 1B:
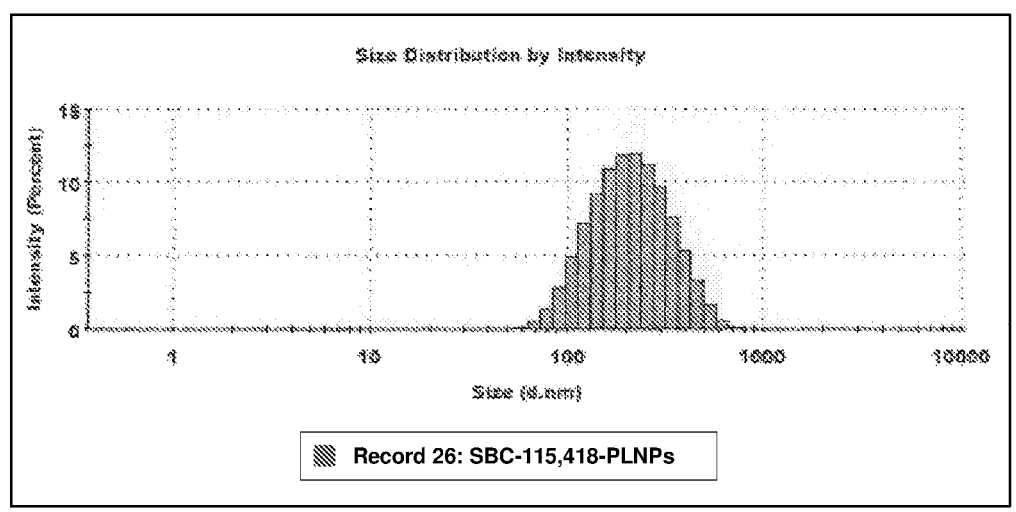
FIG. 1B provides characteristics of the synthesis of SBC-115,418 Nanoformulation E. Formulation E are polymeric lipid nanoparticles (PLNPs) encapsulating SBC-115,418 (PLNPs-SBC-115,418) and was synthesized as described herein. Briefly, 160 mg of lecithin, 40 mg of DSPE-PEG (1, 2-distearoyl-Sn-glycero-3-phosphoethanolamine-N-[amino-(polyethylene glycol)-2000) was dissolved in 20 mL of 4% ethanolic solution. This solution was heated for about 15 minutes at 70° C. Side by side, in another vial, 500 µL of SBC-115,418 (40 mg/mL in Dimethylsufoxide, DMSO), 200 µL of PLGA (80 mg/mL in DMSO), and 200 µL of Mowiol® 15% w/v in DMSO were mixed together. In the next step, both solutions were mixed together under constant magnetic stirring and sonicated for about 2 minutes intermittently using a probe sonicator. Finally, magnetic stirring was applied for about 1 hour at 70° C. (in an open beaker) to evaporate out the ethanol. The entire sample was dialyzed for about 6-8 hours. The dialyzed PLNPs encapsulating SBC-115,418 were lyophilized using 3% sucrose as a cryoprotectant. Lyophilized powder was re-dispersed in deionized (DI) water/PBS for further use. The size distribution of the PLNPs-SBC-115,418 nanoparticles in aqueous dispersions was determined using a Malvern zeta sizer (Malvern Instrumentation Co, Westborough, MA). 50 mg of the lyophilized nanoparticles were re-suspended in 2 mL of DI water. This nanoparticle solution was placed into a 3 mL, 4-sided clear plastic cuvette and measured directly. Shown is the size measure of nanoparticles (formulation E) as determined by a Dynamic Light Scattering (DLS).
Figure 1C:
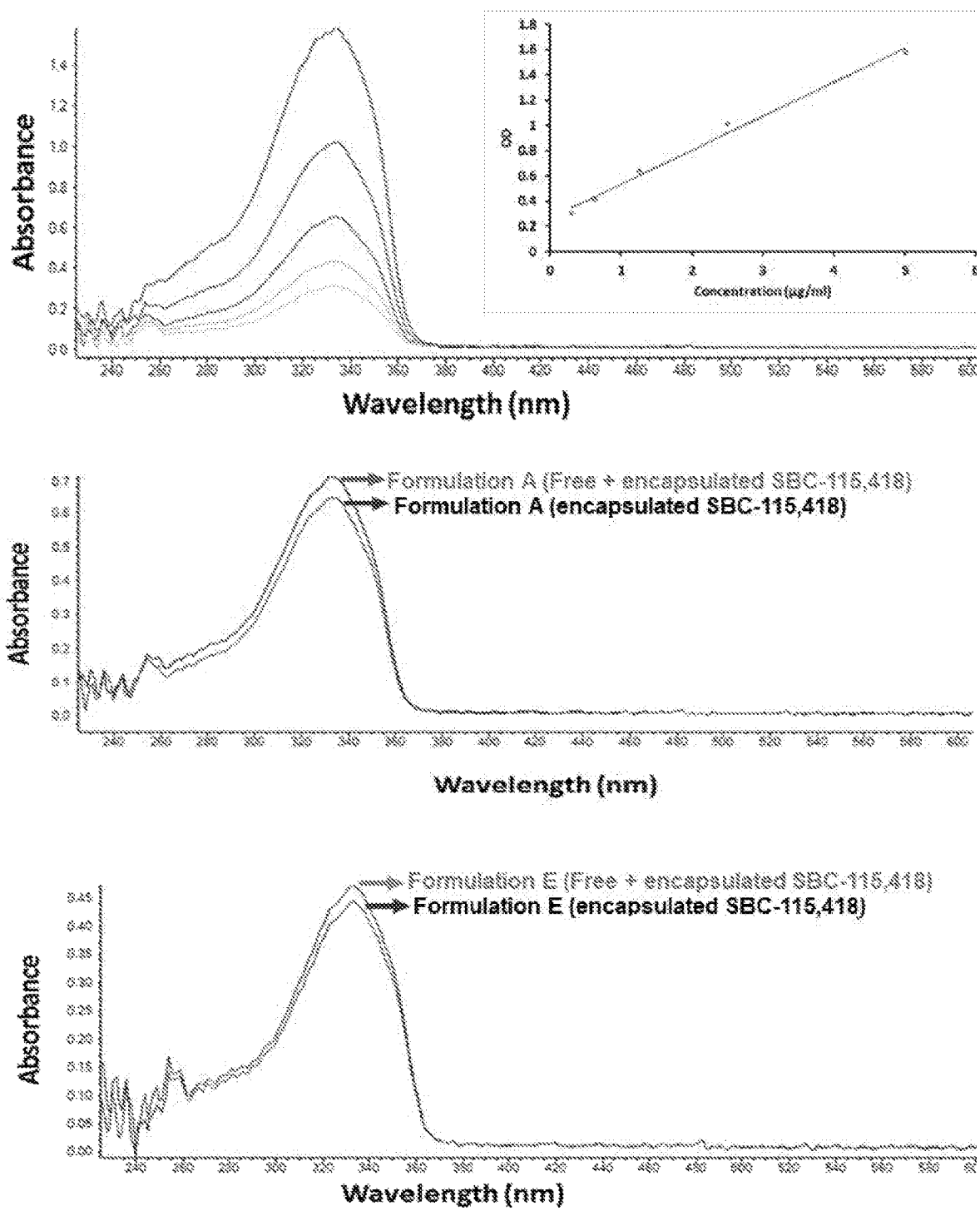
FIG. 1C provides graphs of the Entrapment/Loading efficiency. The amount of SBC-115,418 encapsulated in the nanoparticles (Formulation A & Formulation E) was determined by disintegrating the nanoparticles and using UV-Vis spectroscopy to measure the amount of SBC-115,418 (absorbance at λ 335 nm). The entrapment efficiency was determined with the following formula.
Figure 1D:
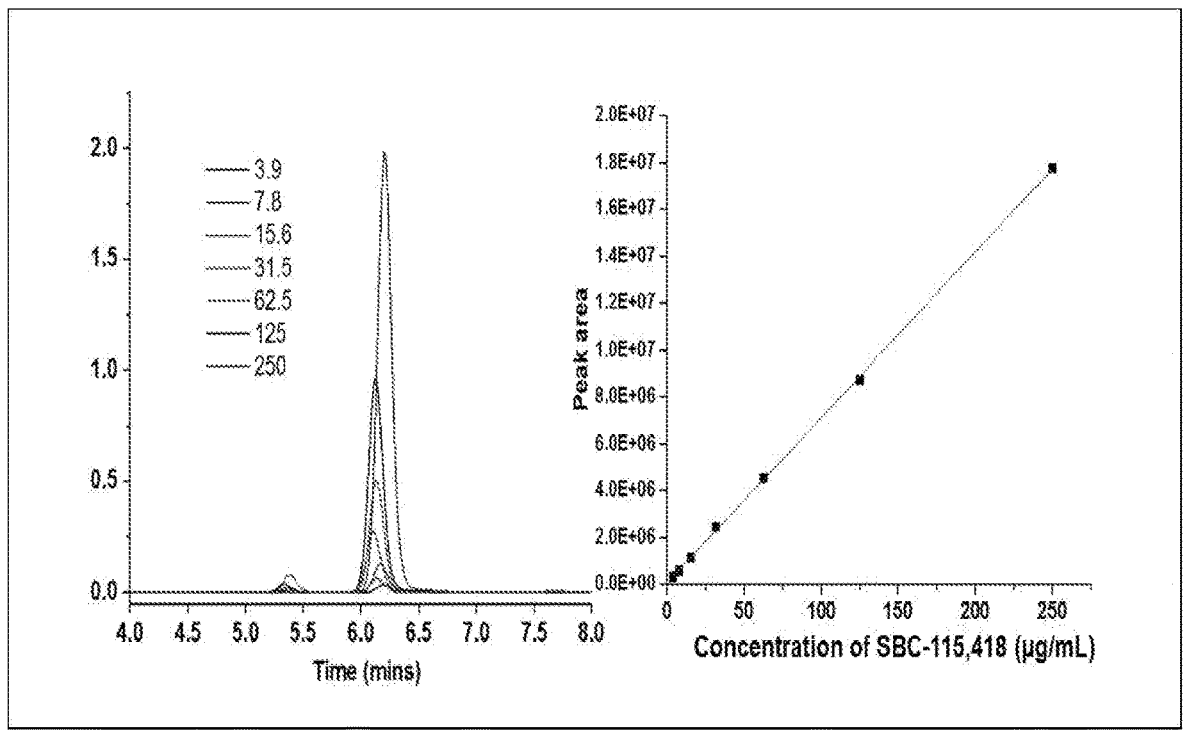

FIG. 1D provides characteristics of SBC-115,418 Nanoformulation D. Shown is the determination of SBC-115,418 encapsulation efficiency and loading rate in Formulation D by HPLC-UV. Nanoparticles were prepared by the nanoprecipitation method. Briefly, for SBC-115,418 drug, an organic solution of SBC-115,418 (10 mg), polyvinyl pyrrolidone (PVP; also referred to as polyvidone or povidone 15 mg; average Molecular Weight 40,000) and Alginic acid (1 mg) in 1 ml DMSO was added to 10 ml of water under magnetic stirring at room temperature. The entire solution was then sonicated for 1-2 minutes using a probe sonicator. Chitosan oligosaccharide lactate (1 mg) was dissolved in 0.5 mL water. This chitosan solution was then added into above entire solution under sonication and incubated for 30 minutes at room temperature. The NP suspension was washed twice with water using centrifugation (15,000×g, 4° C., 60 minutes). Then the NP pellet was frozen at −80° C. for 12 hours, and afterward it was sublimated for 24 hours under pressure of 0.110 mPa at room temperature. Finally, the NPs were collected and preserved in a freezer for pharmacokinetic (PK) and pharmacodynamic (PD) studies. The encapsulation efficiency of SBC-115,418 NPs was determined by analyzing the SBC-115,418 loading in the NPs compared to the SBC-115,418 fed initially. After lyophilization, the weighed NP powder was dispersed in 3 mL of DMSO for 30 minutes. The amount of SBC-115,418 in the DMSO was determined at 337 nm using HPLC and a calibration curve (right). SBC-115,418 encapsulation efficiency was 97% and SBC-115,418 loading was 28% which was calculated from Eqs. 1 and 2, respectively:

$$\text{Entrapment efficiency (\%)} = \frac{\text{weight of SBC-115,418 in nanoparticles}}{\text{weight of SBC-115,418 fed initially}} \times 100 \quad (1)$$

$$\text{SBC-115,418 loading (\%)} = \frac{\text{weight of SBC-115,418 in nanoparticles}}{\text{weight of nanoparticles}} \times 100 \quad (2)$$

The size distribution of the nanoparticles in aqueous dispersions was determined using a Malvern zeta sizer (Malvern Instrumentation Co, Westborough, MA). 50 mg of the lyophilized nanoparticles were re-suspended in 2 mL of water. This nanoparticles solution was placed into a 3 mL, 4-sided, clear plastic cuvette, and measured directly. Shown are the HPLC chromatograms of SBC-115,418 used to construct the standard curve at different concentrations. Calibrator series of SBC-115,418 were prepared in DMSO by a 2-fold series dilution including 3.9, 7.8, 15.6, 31.5, 62.5, 125, and 250 µg/mL (left). 80% Acetonitrile does not fully dissolve 100 µg/mL of SBC-115,418.

Figure 2A:
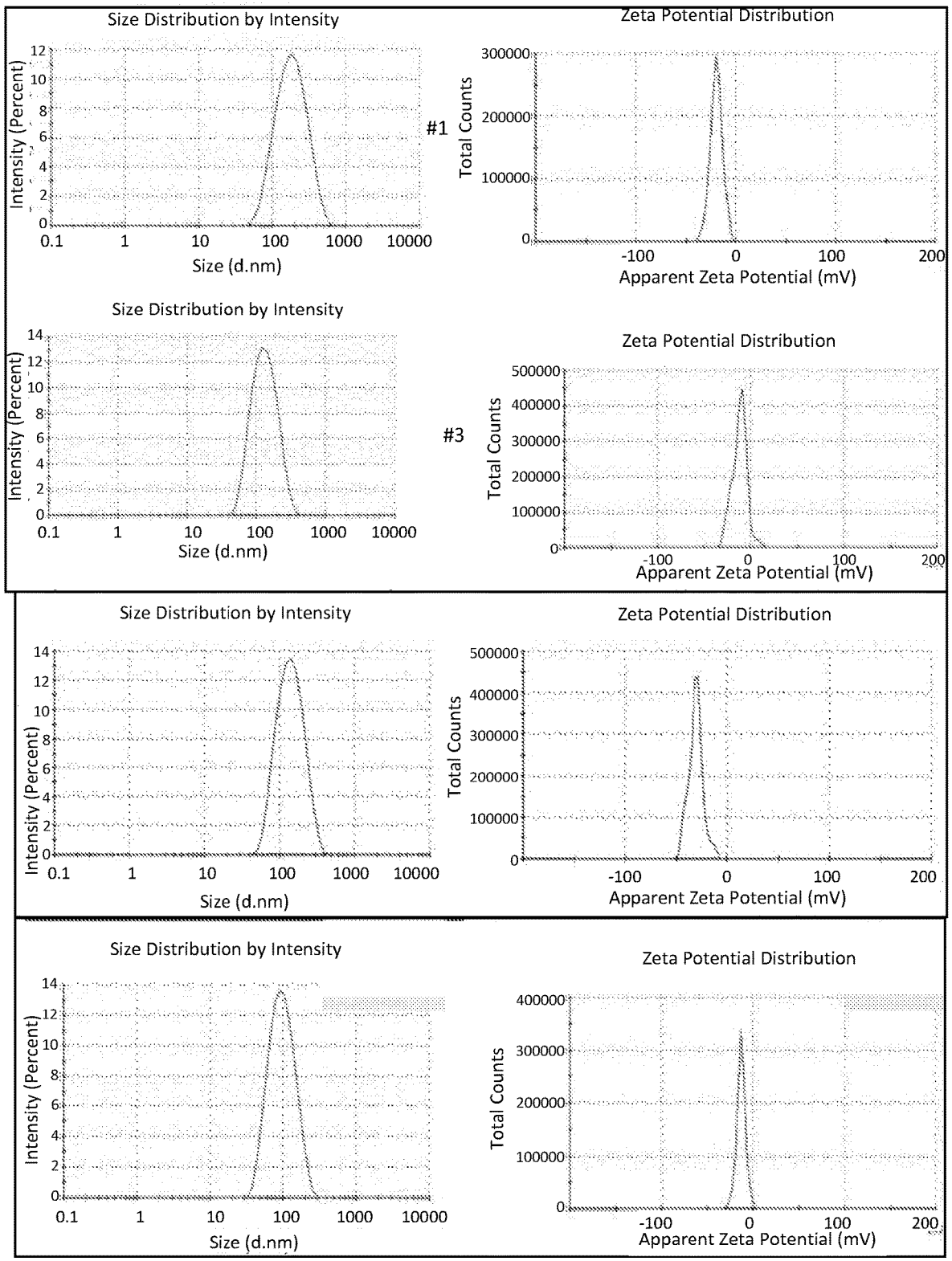

FIG. 2A provides graphs of the size and zeta potential data by DSL for Nanoformulations no.'s 1 and 3 (top). Nanoformulation no. 1 yielded particles with a z-average of 162.4 nm and zeta potential of −19.1 mV. Nanoformulation no. 3 yielded particles with a z-average of 118.5 nm and zeta potential of −11.8 mV. Nanoformulation no. 3 with added mannitol (5%) yielded particles with a z-average of 127.5 nm and zeta potential of −30.8 mV (middle). Nanoformulation no. 4 (8 mg SBC-115,418, 4 mg PVP (40k), 4 mg hydroxypropylmethylcellulose acetate succinate (HPMCAS), 0.6 mg Glycyrrhetinic acid) yielded particles with a z-average of 90.0 nm and zeta potential of −12.8 mV (bottom).

Figure 2B:
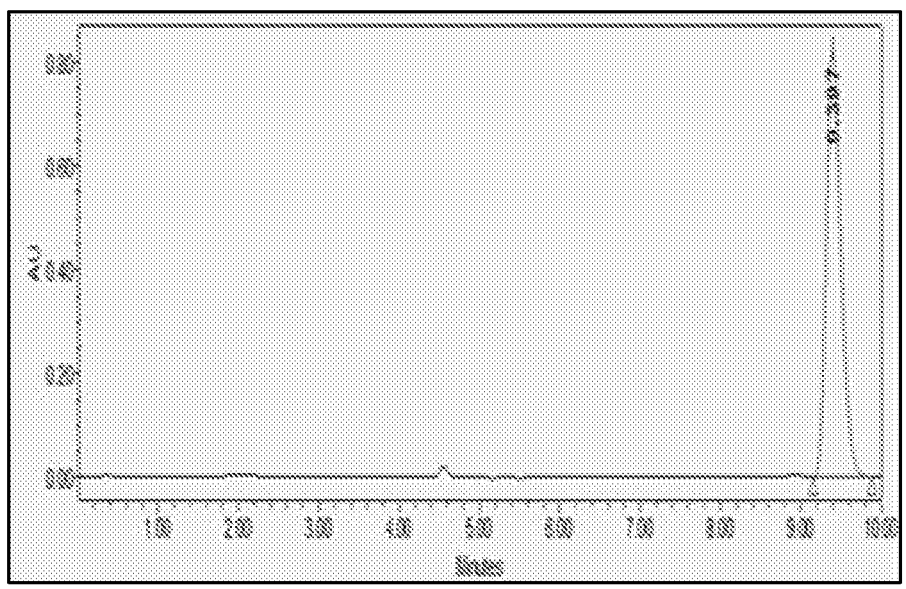
Figure 2B:
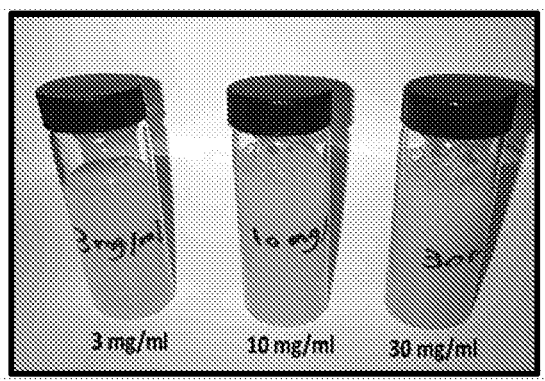

FIG. 2B provides characteristics of a Nanoformulation of SBC-115,418 (Nano SBC-115,418). Briefly, SBC-115,418 (69 mg), PVP (average Molecular Weight 40,000; 69 mg), HPMC-AS (100 mg) and Alginic acid (1 mg) were utilized to synthesize the nanoparticles. SBC-115,418 solutions were analyzed by a HPLC-UV-CAD (top). The SBC-115,418 concentration of the solution was 42 mg/ml. Three concentrations were prepared for in vivo experiment including 30 mg/ml, 10 mg/ml and 3 mg/ml (middle). No significant changes compared to the stock formulation were observed. For efficacy studies, the same formulation was diluted for dosing at 1, 3, 10 and 30 mg/Kg, orally (PO) and 3 mg/Kg, subcutaneous (SC) in mice fed high-fat diet. The nanoparticles also demonstrated good stability (physical and chemical) for the tested period (bottom).

Figure 2C:
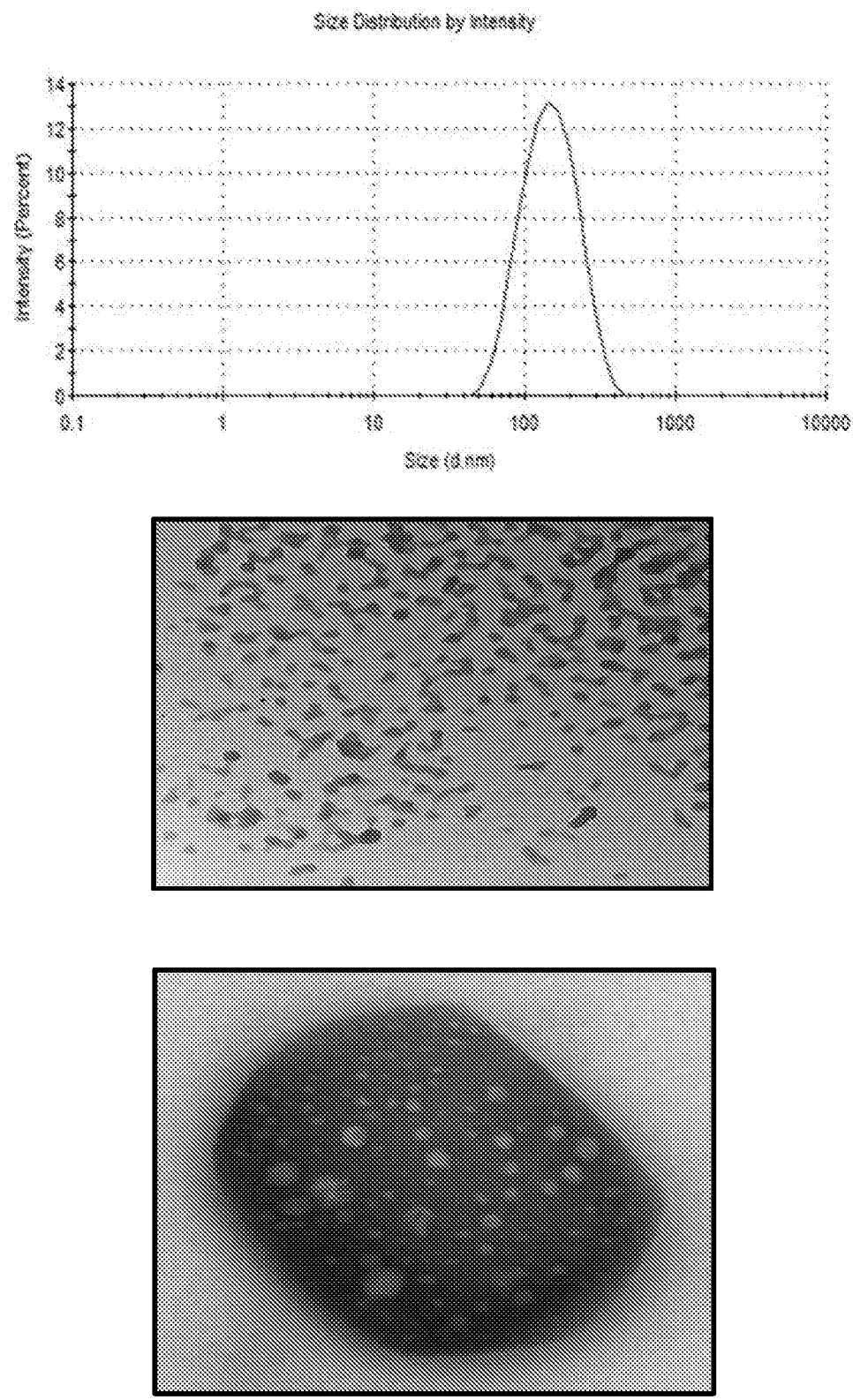

FIG. 2C provides characteristics of Nano SBC-115,418 using Transmission Electron Microscopy (TEM), which indicates that the Zeta size analyzer showing average size of Nanoparticles (Z-average) is 128.2 nm (top). TEM images are also provided confirming the size (50-250 nm) (bottom).

Figure 3:
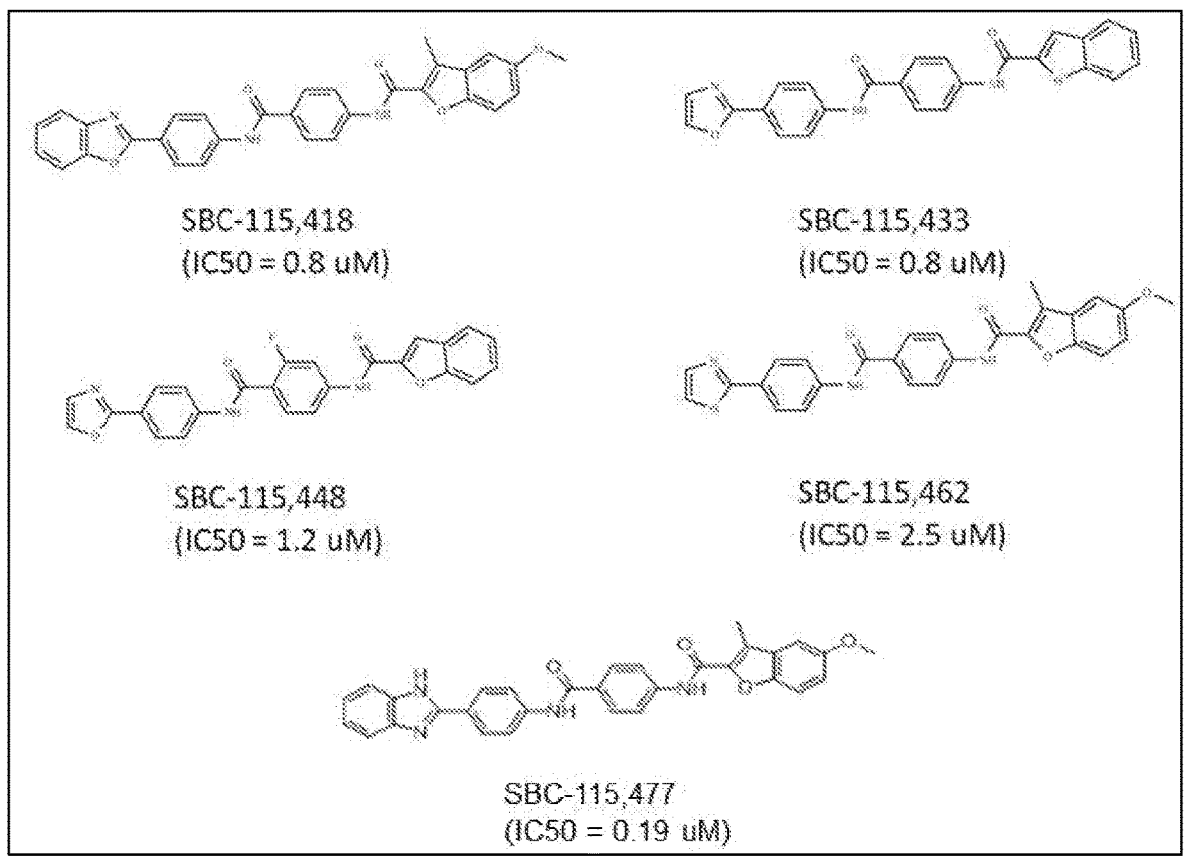

FIG. 3 provides the chemical structures of SBC-115,418, SBC-115,433, SBC-115,448, SBC-115,462 and SBC-115, 477. These compounds (within Formula I and II) effect LDLR upregulation as compared to control while having no significant effect on PCSK9 processing and secretion. The in vitro inhibition of the PCSK9/LDLR interaction (IC$_{50}$, µM) is provided. All are less than 5 µM.

Figure 4A:
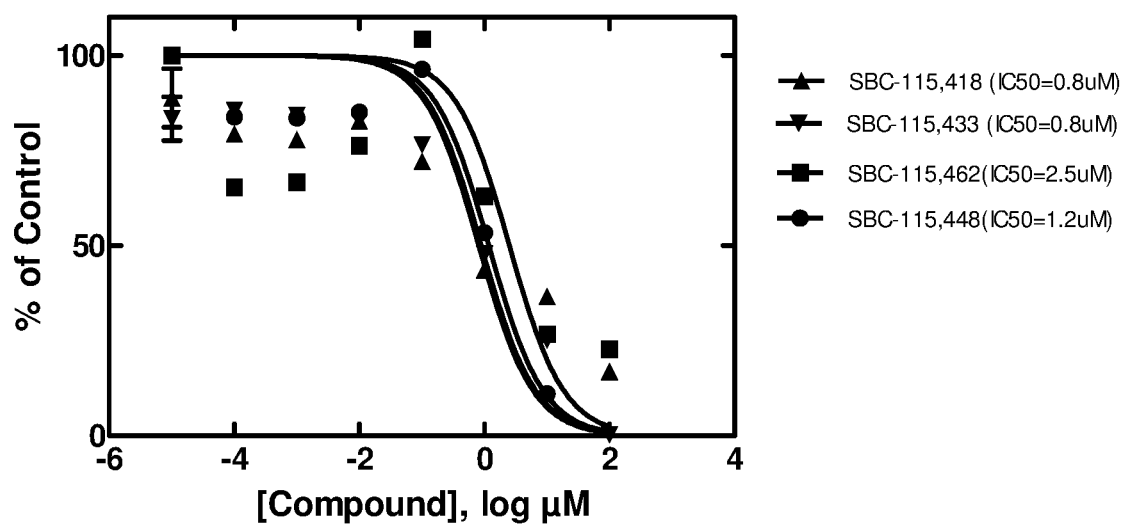

FIG. 4A provides a graph of the effect of SBC-115,418, SBC-115,433, SBC-115,448, and SBC-115,462 on the PCSK9/LDLR interaction. An in vitro ELISA assay kit was utilized (Circulex). For screening inhibitors of the PCSK9/LDLR interaction, different concentrations (0.01 nM-100 µM) of selected compounds were incubated with His-tagged PCSK9 and then added to wells that were pre-coated with recombinant LDLR-AB domain. After incubation, the plate was washed and the amount of recombinant His-tagged PCSK9 was measured using the biotinylated anti-His-tag and horseradish peroxidase conjugated Streptavidin and quantitated using a BioTek Synergy™ 2 plate reader. The effect of each compound on the PCSK9 binding to the recombinant LDLR-AB domain was calculated.

Figure 4B:
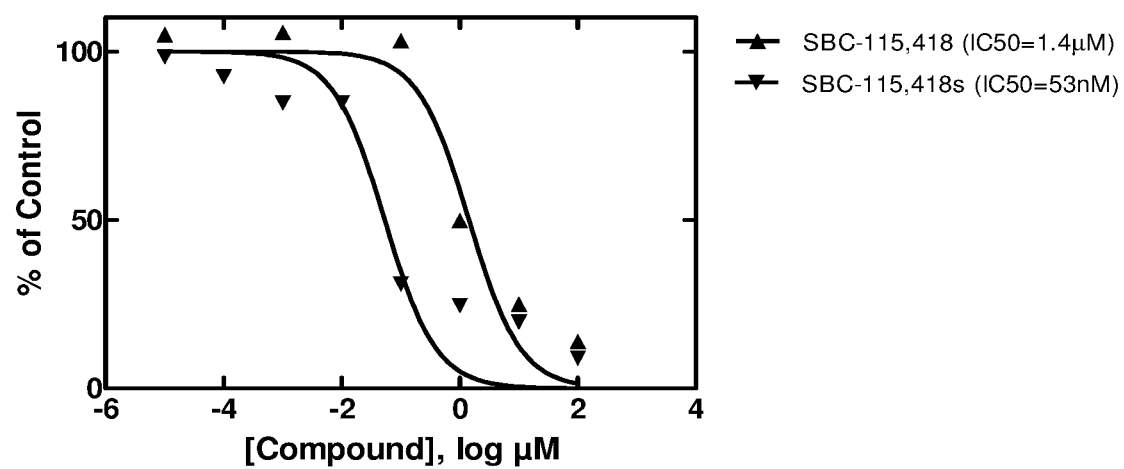

FIG. 4B provides a graph of the effect of SBC-115,418 on the PCSK9/LDLR interaction under increased solubilization conditions (10% DMSO) (418s). An in vitro ELISA assay (Circulex) was utilized. Different concentrations (0.01 γM-100 µM) of SBC-115,418 in DMSO were incubated with His-tagged PCSK9 and then added to wells that were pre-coated with recombinant LDLR-AB domain as described in FIG. 4A.

Figure 5:
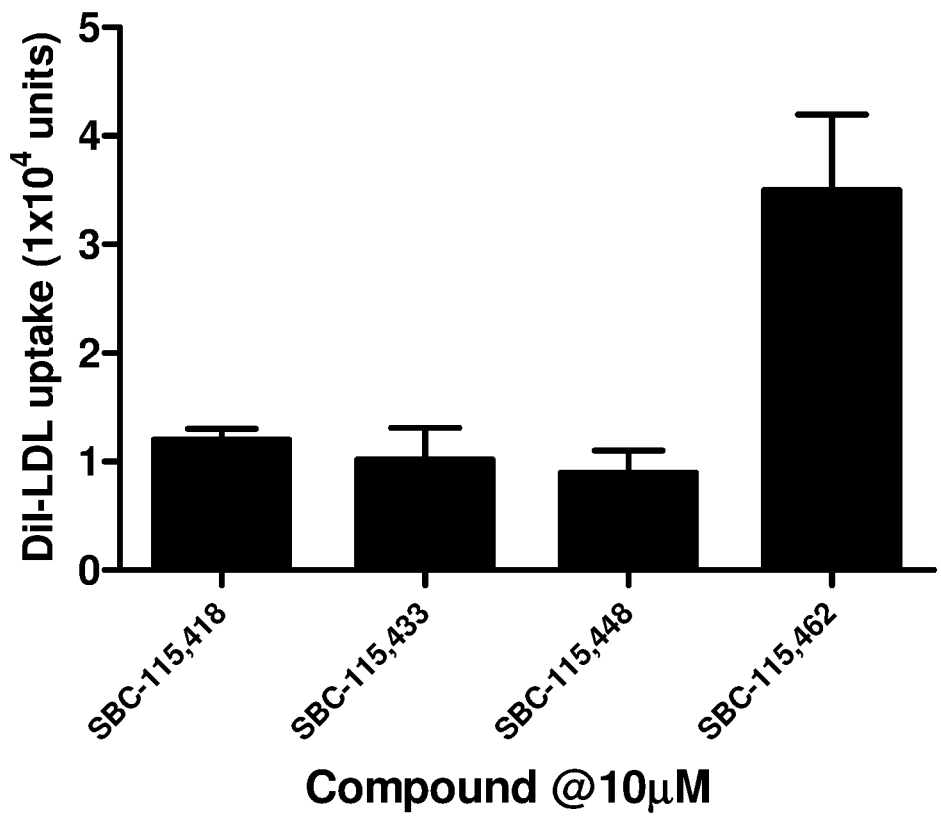

FIG. 5 provides a graph of the effect of SBC-115,418, SBC-115,433, SBC-115,448, and SBC-115,462 on the uptake of fluorescent Dil-LDL in HepG2 Cells. The compounds were validated for their ability to increase uptake of Fluorescent Dil-LDL in HepG2 cells. The data show an increase in the Fluorescent Dil-LDL uptake using 10 µM of the compound.

Figure 6:
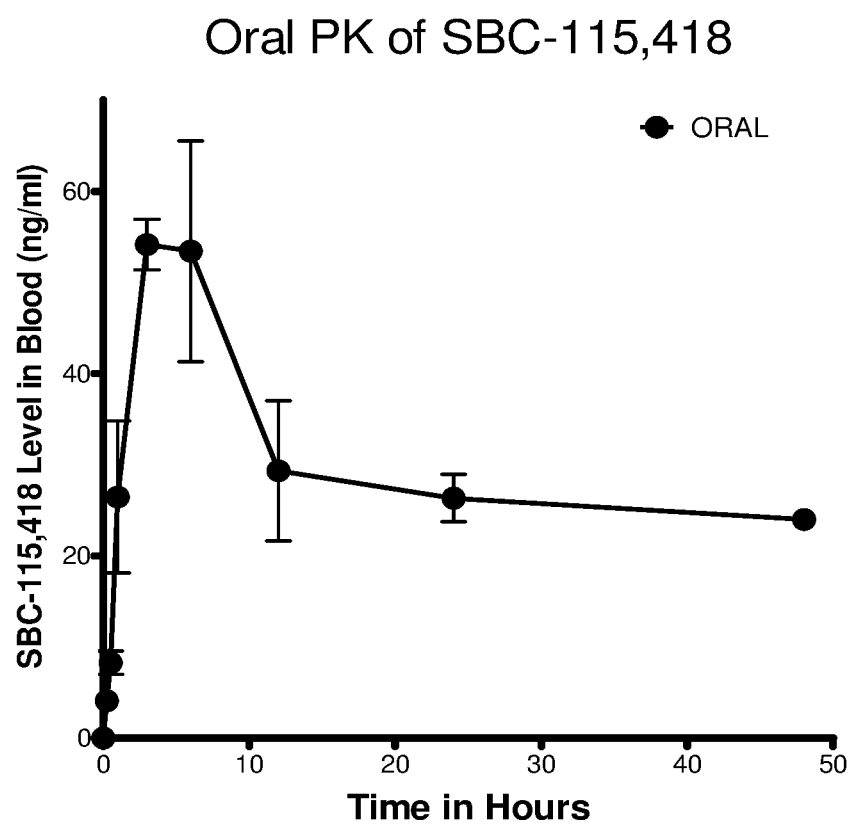

FIG. 6 provides a graph of the PK analysis of Nanoformulation D. Male C57BL/6 mice, 4-5 weeks old were housed 5/cage in a room maintained at 20±2° C. with a humidity of 50±10% and a 12 hour light/dark cycle. The animals were fed a standard pelleted mouse chow. Single intravenous (IV) (10 mg/kg) and oral (30 mg/kg) dose of SBC-115,418 Formulation D were administered and 50 µl of blood samples were collected using anti-coagulated capillary tubes at 0.25, 0.5, 1, 3, 6, 12, 24 and 48 hours post-administration for PK profiles using established LC/MS/MS method. An internal standard was used to correct for extraction efficiency. Compound concentration in the plasma is expressed as ng/ml. The data shows an increased concentration of the compound was observed after 30 minutes of administration with 18% oral bioavailability relative to IV for SBC-115,418 and longer half-life.

Figure 7:
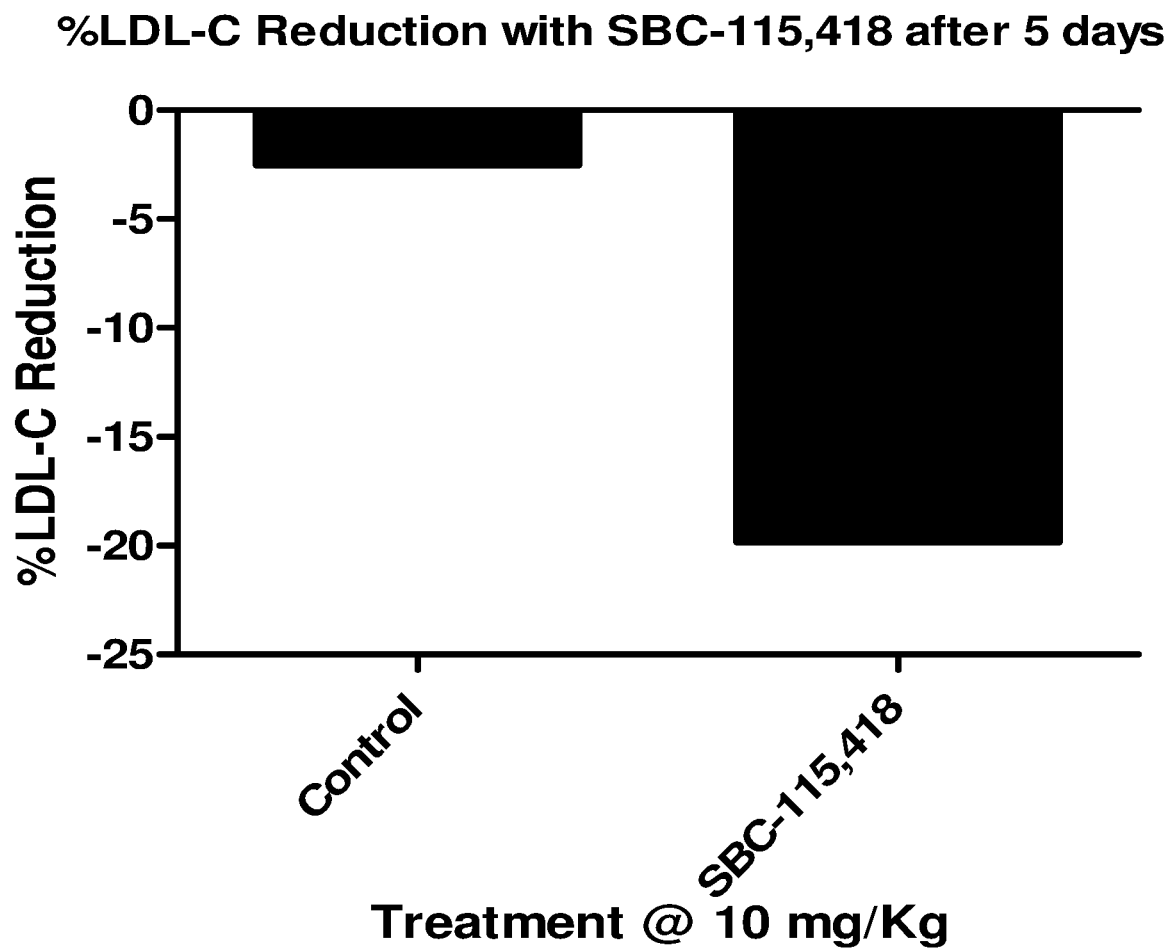

FIG. 7 provides a graph of the PD analysis of Nanoformulation D. SBC-115,418 in Formulation D was tested for efficacy in male mice (C57BL/6 mice). Mice were housed at four animals per cage under climate-controlled conditions of temperature (20-24° C.), humidity (60-70%), and alternating 12 hour light/dark cycles. The mice were divided into 3 groups. One group was fed commercial chow diet (Prolab RMH 3000, PMI feeds, St. Louis, MO) to serve as a negative control, while the other 2 groups were fed high-fat diet (TD.06414), which provides 60% of calories from fat. Water was provided ad libitum. Plasma was collected once weekly to monitor the level of LDL. After 4 weeks of feeding a high-fat diet, mice were randomly assigned to one of several groups such that the average LDL levels were equal among different groups. One of the 2 groups of mice fed high-fat diet was treated with vehicle and served as a positive control, whereas the second group was treated daily with 10 mg/kg of SBC-115,418 orally for 5 days. Blood samples (75 µl) were collected 5 days after drug administration from the retro-orbital venous plexus via heparinized capillary tubes containing 2 USP units of ammonium heparin per tube (Carolina, Burlington, NC). Plasma was separated immediately by centrifugation (5,000×g) for 5 minutes at room temperature and then kept at −80° C. until assayed for lipid profile. Plasma cholesterol and LDL-C levels were measured enzymatically.

Figure 8:
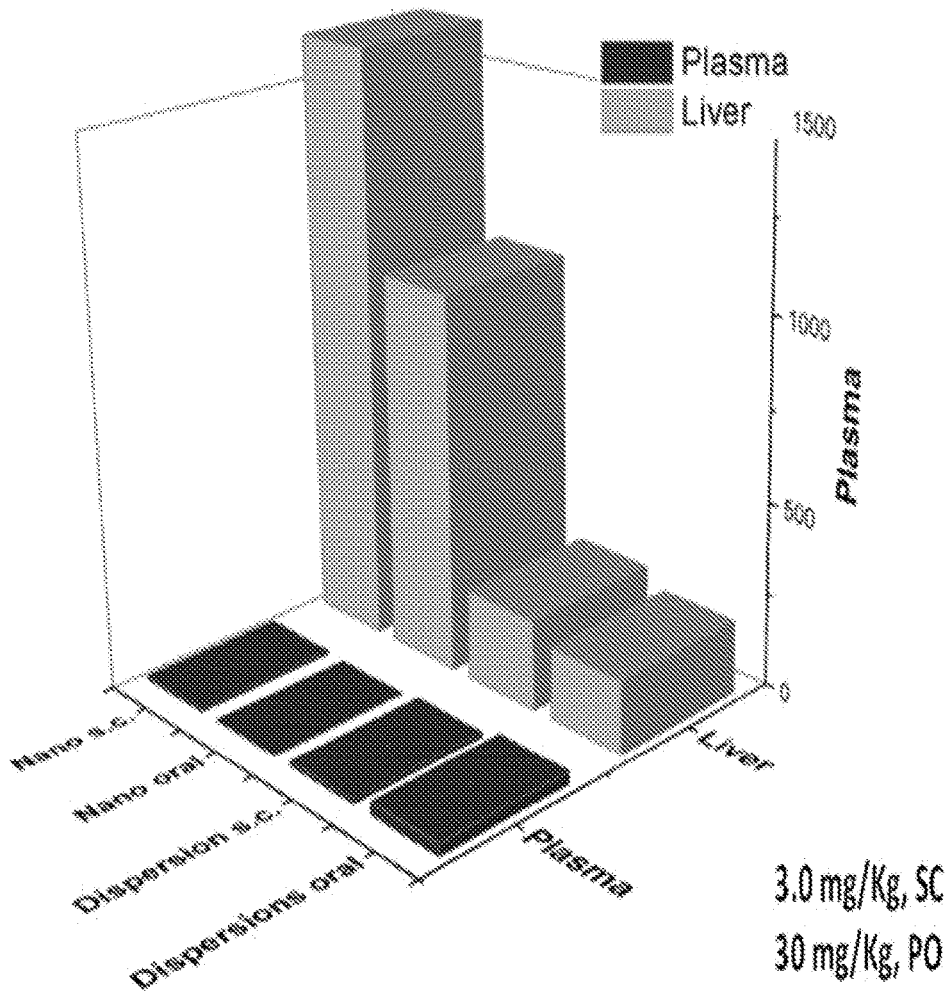

FIG. 8 provides a graph of the measured SBC-115,418 levels in both plasma and the liver at 24 hours after administration of Nano SBC-115,418 in mice fed a high-fat diet versus the dispersion formulation. Liver tissues were weighed and homogenized in organic solvents at 1:1:1 ratio of DMSO/Acetonitrile/Methanol along with reserpine as an internal standard. Tissue homogenates were centrifuged at 15,000×g for 15 minutes and supernatant was lyophilized and reconstituted in a small but known volume of acetonitrile for injection into the LC/MS/MS.

Figure 9:
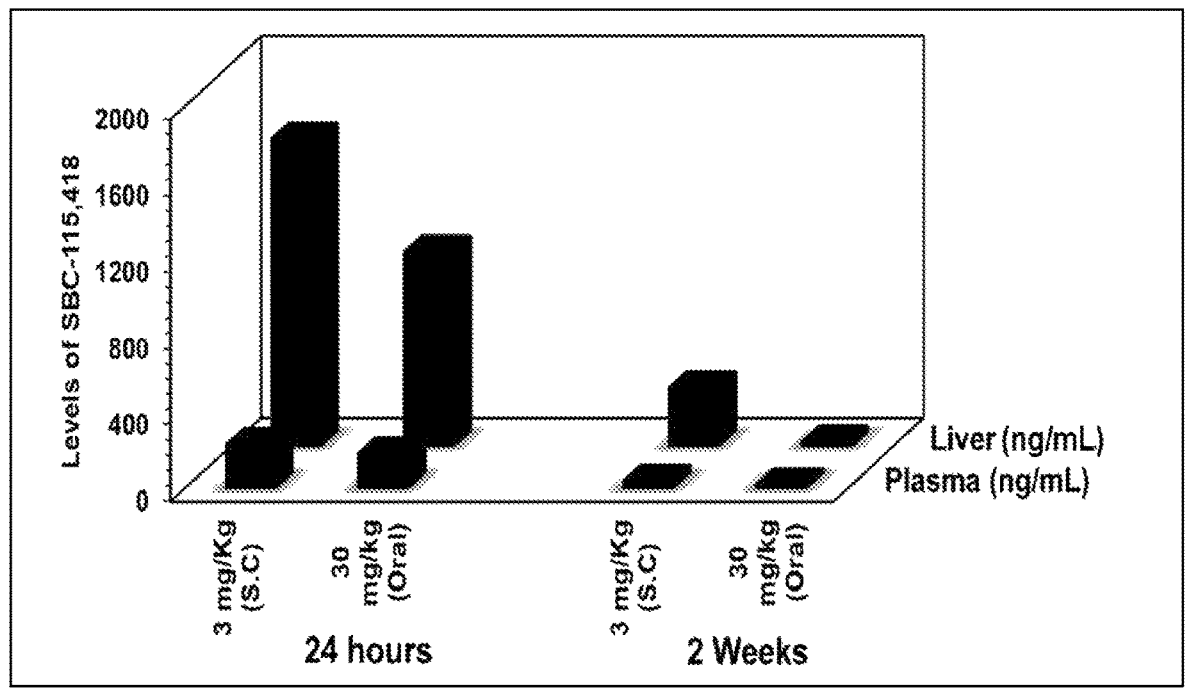

FIG. 9 provides a graph of SBC-115,418 levels at 24 hours and 2 weeks after daily administration of Nano SBC-115,418 in mice fed high-fat diet. The hepatic-targeted delivery of Nano SBC-115,418 shows the adjustment of liver levels (2 weeks) after repeated dosing without significant accumulation of drug but with enough residual levels for sustained effects.

Figure 10:
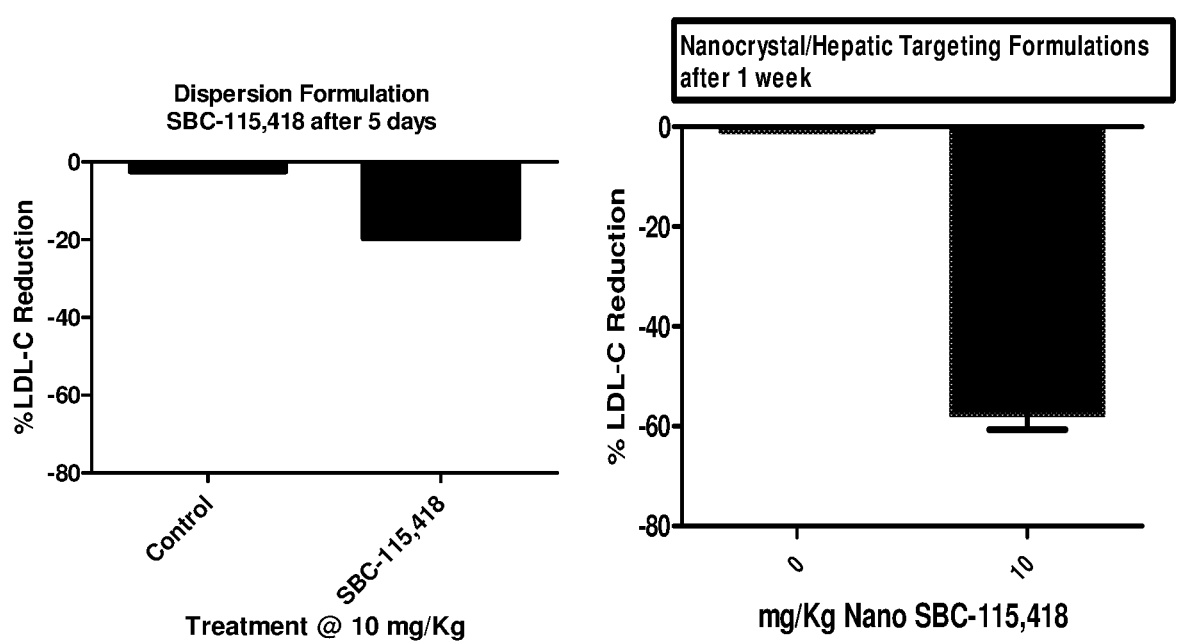

FIG. 10 provides graphs of LDL-cholesterol reduction with the Dispersion Formulation of SBC-115,418 (left) versus Nanocrystal/Hepatic Targeting Formulation (Nano SBC-115,418) (right) in C57BL/6 mice fed high-fat diet. C57BL/6 mice received 10 mg/kg oral daily for 5 days (Dispersion) or 7 days (Nano SBC-115,418). Blood plasma was collected at the indicated time and plasma LDL-C levels were measured. The graph shows greater efficacy of Nano SBC-115,418 (~60% LDL-lowering) versus the Dispersion Formulation of SBC-115,418 (~20% LDL-lowering).

Figure 11:
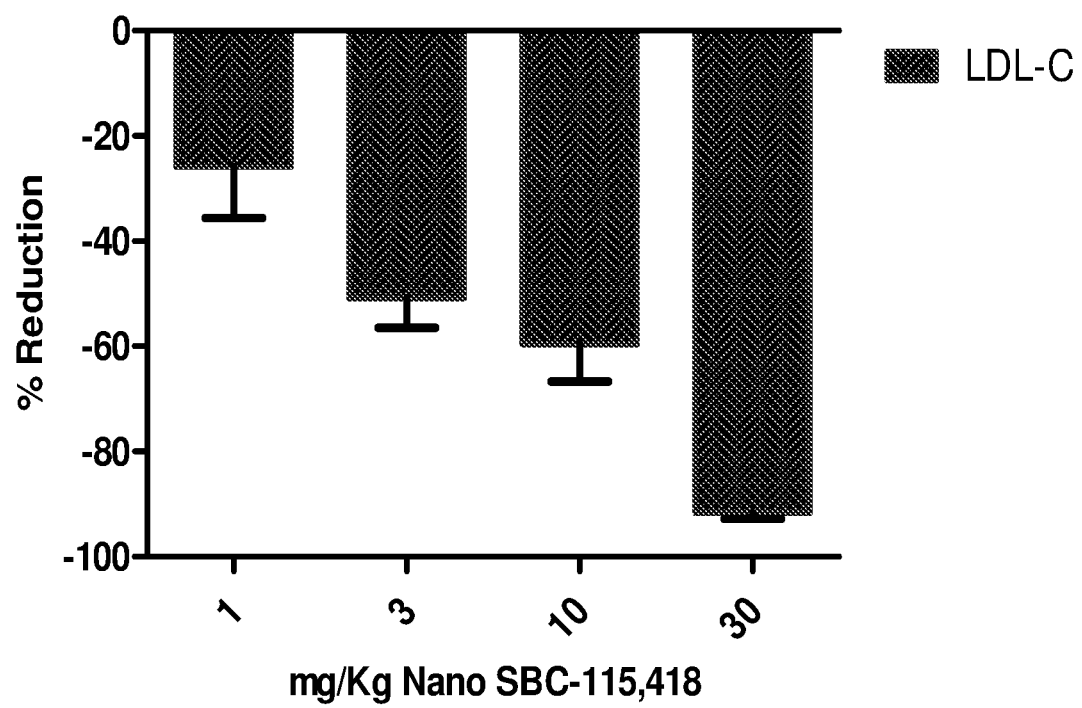

FIG. 11 provides a graph of the level of LDL-cholesterol in plasma of mice fed high-fat diet treated with Nano SBC-115,418 for 2 weeks.

Figure 12:
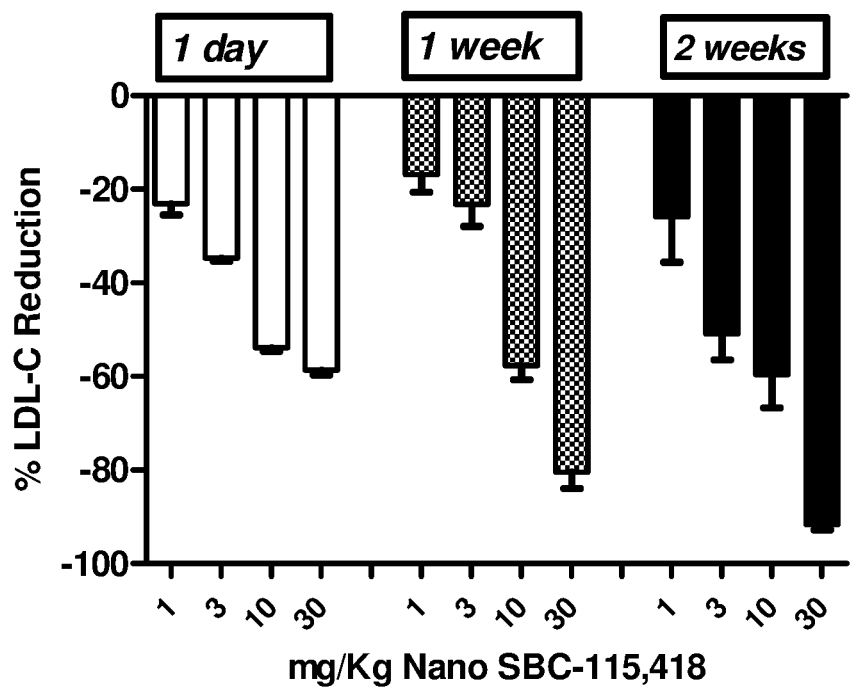

FIG. 12 provides a graph of the level of LDL-cholesterol in plasma of mice fed high-fat diet treated with different dosages of Nano SBC-115,418 for 1-day, 1-week and 2-weeks.

Figure 13:
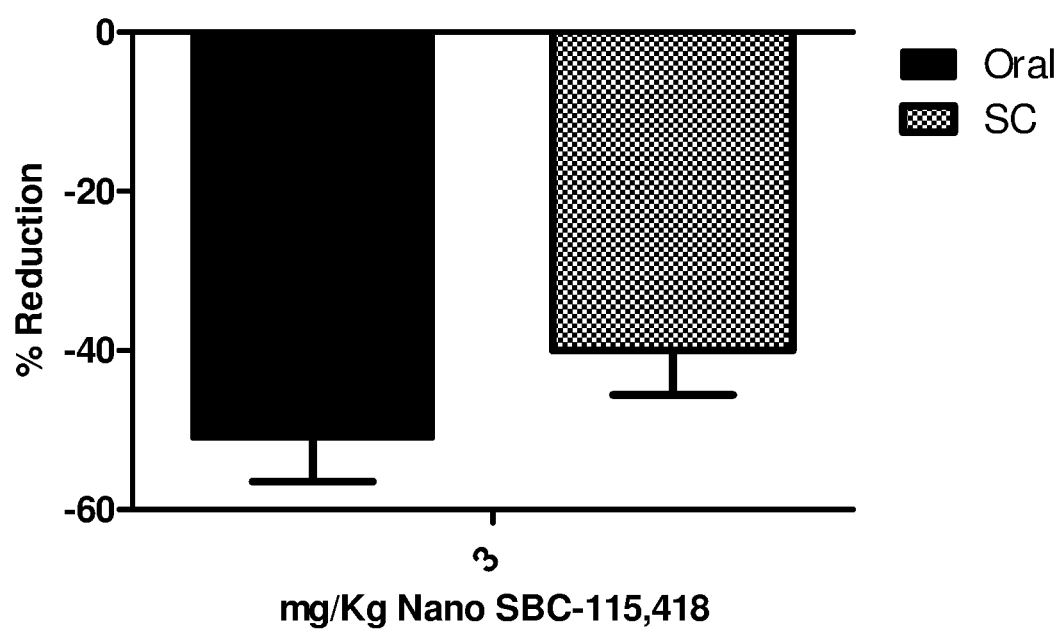

FIG. 13 provides a graph of the level of plasma LDL-cholesterol in high-fat diet mice treated either orally or by subcutaneous injection with 3 mg/Kg of Nano SBC-115, 418.

Figure 14:
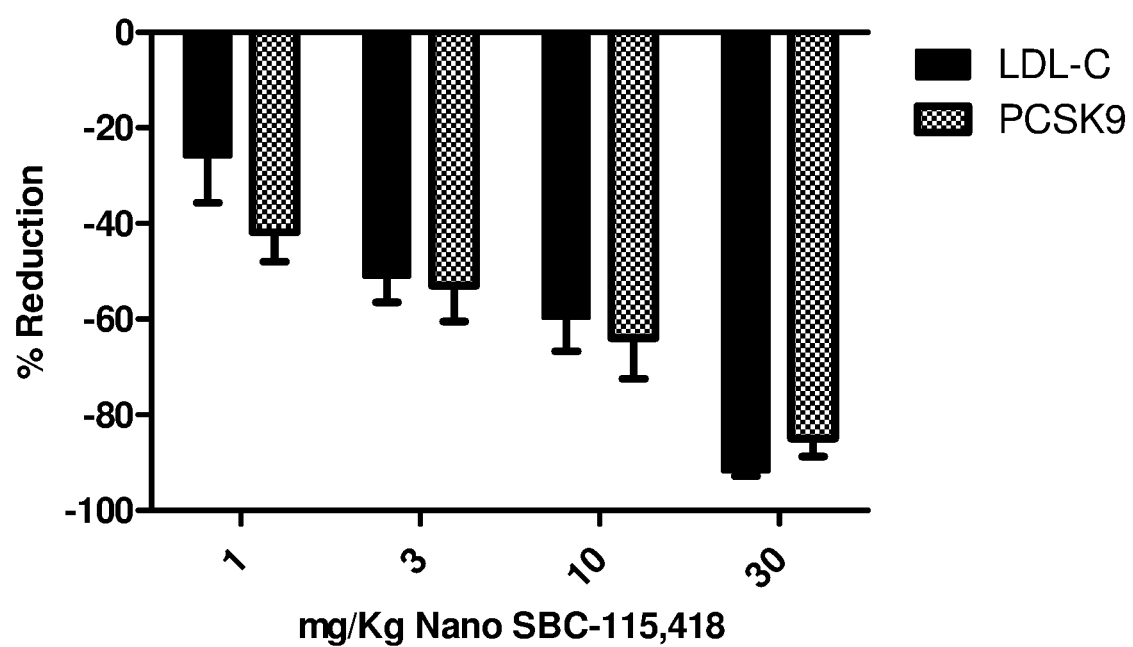

FIG. 14 provides a graph showing the effect of Nano SBC-115,418 on plasma LDL-C and PCSK9 levels in C57/Black6 mice fed high-fat diet.

Figure 15:
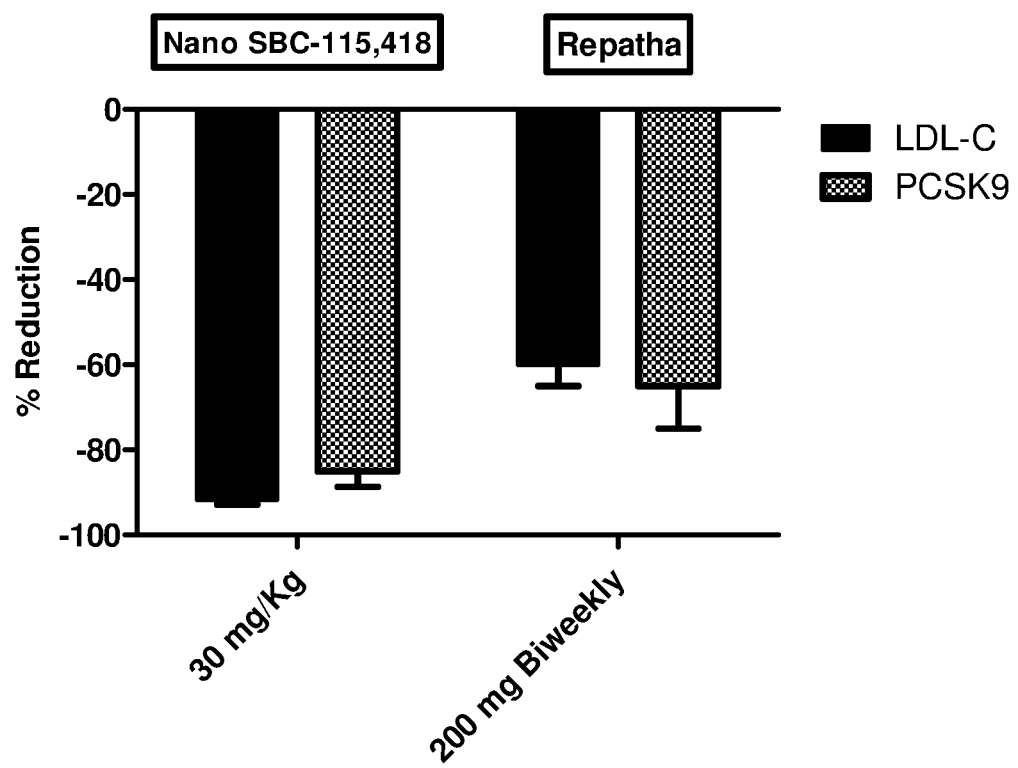

FIG. 15 provides a graph showing the comparison between the effect of oral Nano SBC-115,418 (30 mg/Kg, 2 weeks) in C57/Black6 mice fed high-fat diet and injectable Repatha® (200 mg Biweekly) in humans on plasma LDL-C and PCSK9 levels.

Figure 16:
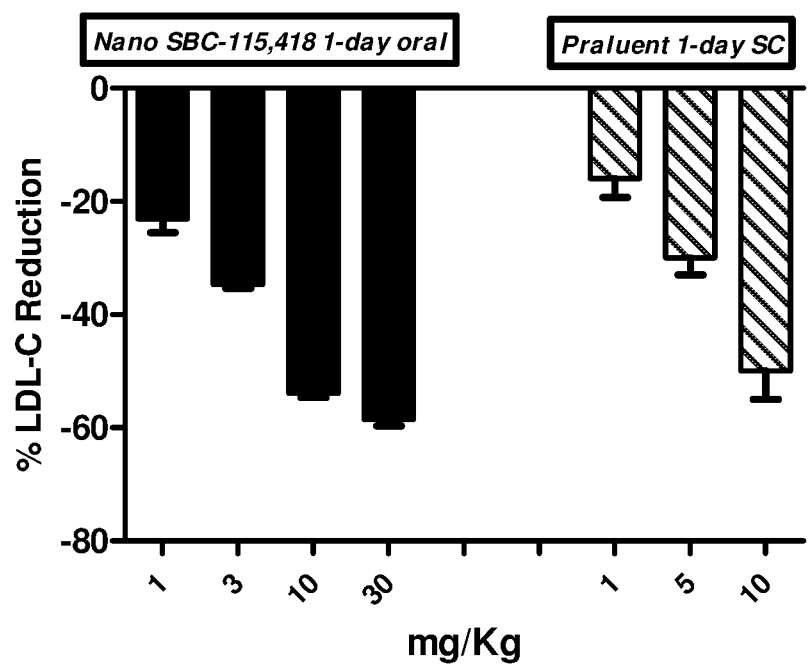

FIG. 16 provides a graph showing the comparison between the effect of oral Nano SBC-115,418 (30 mg/Kg, 1 day) in C57/Black6 mice fed high-fat diet and SC injectable of Praluent® (200 mg, 1 day) in mice on plasma LDL-C and PCSK9 levels.

Figure 17:
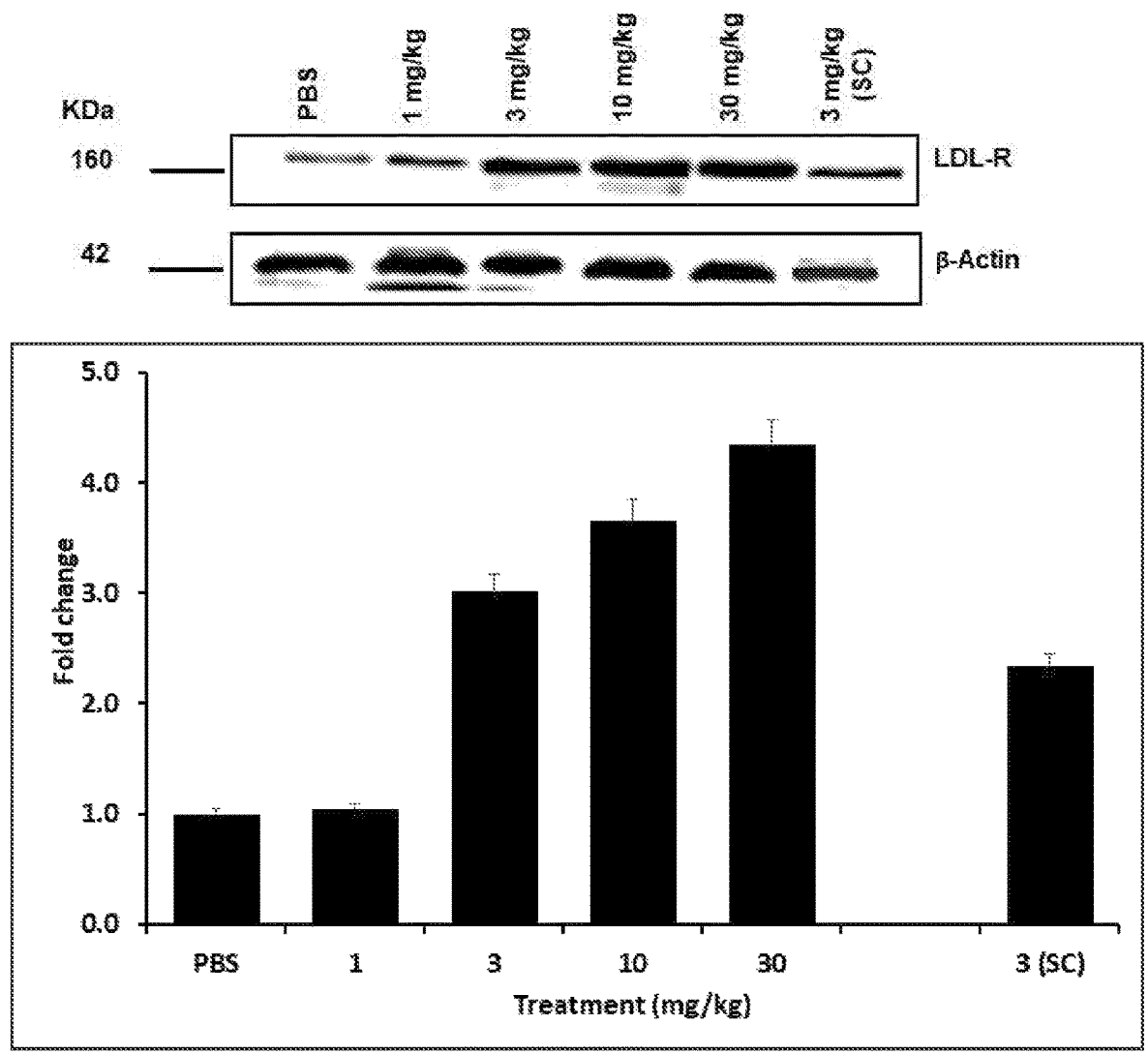

FIG. 17 provides a Western blot analysis (top) and a graph (bottom) showing the levels of LDL receptor expression in livers of mice fed high-fat diet treated with different dosages of Nano SBC-115,418.

DETAILED DESCRIPTION OF THE INVENTION

The present invention provides potent LDL-lowering agents and methods of use thereof including Nano-hepatic targeting approaches. To improve the efficacy of small molecule PCSK9/LDLR antagonists, the present invention uses a nanotechnology platform to target PCSK9 antagonists such as SBC-115,418 and its analogs, with or without statin or other LDL-C lowering agents, for differential targeted delivery to the liver in order to maximize efficacy and minimize its systemic distribution. FIGS. 1 and 2 depict selected examples of nanoparticles comprising SBC-115, 418 and hepatic targeting moieties (Glycyrrhetinic acid (GA), Lactobionic acid (LA) and Alginic acid), in accordance with embodiments of the present invention. As demonstrated herein, Nanoformulations of PCSK9 antagonists such as SBC-115,418 and its analogs modified for hepatic targeting provide improved efficacy in lowering LDL-cholesterol. Unlike the statin class of drugs which decrease cholesterol synthesis, PCSK9 antagonists such as SBC-115,418 and its analogs down regulate the function of extracellular proprotein convertase subtilisin kexin type 9 (PCSK9), including its interaction with the low density lipoprotein (LDL) receptor (LDLR). PCSK9 antagonists and nanoformulations thereof can be used therapeutically to lower LDL-cholesterol levels in blood and in the prevention and/or treatment of cholesterol and lipoprotein metabolism disorders, including familial hypercholesterolemia, atherogenic dyslipidemia, atherosclerosis, and, more generally, cardiovascular disease (CVD).

Nano-hepatic targeted PCSK9 antagonists (e.g., SBC-115,418) of the instant invention can be combined with a statin or other lipid lowering substance. In a particular embodiment, the drugs (e.g., PCSK9 antagonist and lipid lowering (e.g., LDL-lowering) substance) are Nano-encapsulated into hydrophobic nanoparticles. Examples of hydrophobic nanoparticles include, without limitation, amine-modified poly-(lactic-co-glycolic acid) (PLGA), docosahexaenoic acid (DHA), eicosapentaenoic acid (EPA), or EPA/DHA, or solid lipid nanoparticles (SLNs) using HDL with or without cross-linkage or grafting to chitosan. Chitosan, particularly low to ultralow molecular weight chitosan, may be conjugated to fatty acids (including, but not limited to, EPA, DHA, and/or combinations in different amounts) or other acids (e.g., amino acids, hyaluronic acid, and/or linoleic acids), leading to the generation of a hydrophobic polymer that still retains mucoadhesive properties and positive charges for long residence time on cell membranes. Encapsulation of SBC-115,418 into hydrophobic PLGA with or without chitosan and polyethylene glycol (PEG), chitosan-EPA, chitosan-DHA or chitosan-EPA/DHA nanoparticles, as well as SLNs conjugated to hepatic targeting moieties such as Glycyrrhetinic acid, Lactobionic acid, and Alginic acid are exemplified hereinbelow.

As used herein, the term "subject" includes both humans and animals. As used herein, the term "PCSK9" refers to any form of the protein PCSK9, including PCSK9 mutants and variants, which retain at least part of PCSK9 activity or function. Unless otherwise indicated, such as by specific reference to human PCSK9, PCSK9 refers to all mammalian species of native sequence PCSK9, e.g., human, porcine, bovine, equine, canine and feline. One exemplary human PCSK9 sequence is found as Uniprot Accession Number Q8NBP7. An exemplary amino acid sequence is:

```
                                         (SEQ ID NO: 1)
MGTVSSRRSW WPLPLLLLLL LLLGPAGARA QEDEDGDYEE

LVLALRSEED GLAEAPEHGT TATFHRCAKD PWRLPGTYVV

VLKEETHLSQ SERTARRLQA QAARRGYLTK ILHVFHGLLP

GFLVKMSGDL LELALKLPHV DYIEEDSSVF AQSIPWNLER
```

-continued

```
ITPPRYRADE YQPPDGGSLV EVYLLDTSIQ SDHREIEGRV

MVTDFENVPE EDGTRFHRQA SKCDSHGTHL AGVVSGRDAG

VAKGASMRSL RVLNCQGKGT VSGTLIGLEF IRKSQLVQPV

GPLVVLLPLA GGYSRVLNAA CQRLARAGVV LVTAAGNFRD

DACLYSPASA PEVITVGATN AQDQPVTLGT LGTNFGRCVD

LFAPGEDIIG ASSDCSTCFV SQSGTSQAAA HVAGIAAMML

SAEPELTLAE LRQRLIHFSA KDVINEAWFP EDQRVLTPNL

VAALPPSTHG AGWQLFCRTV WSAHSGPTRM ATAVARCAPD

EELLSCSSFS RSGKRRGERM EAQGGKLVCR AHNAFGGEGV

YAIARCCLLP QANCSVHTAP PAEASMGTRV HCHQQGHVLT

GCSSHWEVED LGTHKPPVLR PRGQPNQCVG HREASIHASC

CHAPGLECKV KEHGIPAPQE QVTVACEEGW TLTGCSALPG

TSHVLGAYAV DNTCVVRSRD VSTTGSTSEG AVTAVAICCR

SRHLAQASQE LQ.
```

As used herein, a "modulator of PCSK9 function" refers to a small molecule that is able to inhibit PCSK9 biological activity or function, and/or downstream pathway(s) mediated by PCSK9 signaling, including PCSK9-mediated down-regulation of the LDLR, and PCSK9-mediated inhibition of the decrease in LDL blood clearance. A modulator of PCSK9 function encompasses compounds that block, antagonize, suppress or reduce (to any degree including significantly) PCSK9 biological activity, including downstream pathways mediated by PCSK9 signaling, such as LDLR interaction and/or elicitation of a cellular response to PCSK9. For purpose of the present invention, it will be explicitly understood that the term "modulator of PCSK9 function" encompasses all the previously identified terms, titles, and functional states and characteristics whereby the PCSK9 itself, a PCSK9 biological activity (including but not limited to its ability to mediate any aspect of interaction with the LDLR, down regulation of LDLR, and inhibit the decrease in blood LDL clearance), or the consequences of the biological activity, are substantially nullified, decreased, or neutralized in any measurable degree. In some embodiments, a modulator of PCSK9 function binds PCSK9 and prevents its interaction with the LDLR or its secretion. In other embodiments, a modulator of PCSK9 function binds to the active site of PCSK9 to stabilize its zymogen and prevent auto-processing. In further embodiments, a modulator of PCSK9 function decreases or blocks PCSK9 mediated down-regulation of the LDLR; inhibits the PCSK9-mediated decrease in LDL blood clearance; increases LDL clearance in media by cultured hepatocytes; increases blood LDL clearance by the liver in vivo; improves patients' sensitivity to other LDL lowering drugs, including statins; is synergistic to other LDL lowering drugs, including statins; and blocks PCSK9 interaction with other yet to be identified factors. Examples of modulators of PCSK9 function are provided herein. In a particular embodiment, the "modulator of PCSK9 function" is a PCSK9 antagonist.

The compounds of the instant invention can be administered as salts, which are also within the scope of this invention. Pharmaceutically acceptable (i.e., non-toxic, physiologically compatible) salts are preferred. If the compounds of the method of the present invention have, for example, at least one basic center, they can form acid addition salts. These can be formed, for example, with strong inorganic acids, such as mineral acids, for example sulfuric acid, phosphoric acid or a hydrochloric acid, with strong organic carboxylic acids, such as alkane carboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxyl carboxylic acids, for example ascorbic, glycolic, lactic, malic, tartaric or citric acid, such as amino acids, for example aspartic or glutamic acid or lysine or arginine, or benzoic acid, or with organic sulfonic acids, such as ($C_1$-$C_4$) alkyl or arylsulfonic acids which are unsubstituted or substituted, for example by halogen, for example methyl- or para-toluene-sulfonic acid. Corresponding acid addition salts can also be formed having plural basic centers, if desired. The compounds used in the method of the present invention having at least one acid group (for example COOH) can also form salts with suitable bases. Representative examples of such salts include metal salts, such as alkali metal or alkaline earth metal salts, for example sodium, potassium or magnesium salts, or salts with ammonia or an organic amine, such as morphine, thiomorpholine, piperidine, pyrrolidine, a mono, di- or tri-lower alkylamine, for example ethyl, tert-butyl, diethyl, diisopropyl, triethyl, tributyl or dimethyl-propylamine, or a mono, di- or trihydroxy lower alkylamine, for example mono, di- or triethanolamine. Corresponding internal salts may also be formed.

Exemplary salts of the compounds described herein, which contain a basic group, include monohydrochloride, hydrogensulfate, methanesulfonate, phosphate or nitrate.

Exemplary salts of the compounds described herein, which contain an acid group, include sodium, potassium and magnesium salts and pharmaceutically acceptable organic amines.

All stereoisomers of the compounds, which may be used in the methods described herein, either in a mixture or in pure or substantially pure form, are considered to be within the scope of this invention. The compounds of the present invention can have asymmetric centers at any of the carbon atoms including any one of the R substituents. Consequently, compounds used in the method of the invention can exist in enantiomeric or diastereomeric forms or in mixtures thereof. The processes for preparation of such compounds can utilize racemates, enantiomers or diastereomers as starting materials. When diastereomeric or enantiomeric products are prepared, they can be separated by conventional methods, for example chromatographic, chiral HPLC or fractional crystallization.

As used herein, the term "pharmacophore" refers to the ensemble of steric and electronic features that are necessary to ensure the optimal supramolecular interactions with a specific biological target structure and to trigger, activate, block, inhibit or modulate the biological target's biological activity, as the case may be. See, IUPAC, *Pure and Applied Chemistry* (1998) 70: 1129-1143.

As used herein, the term "pharmacophore model" refers to a representation of points in a defined coordinate system wherein a point corresponds to a position or other characteristic of an atom or chemical moiety in a bound conformation of a ligand and/or an interacting polypeptide, protein, or ordered water molecule. An ordered water molecule is an observable water in a model derived from structural determination of a polypeptide or protein. A pharmacophore model can include, for example, atoms of a bound conformation of a ligand, or portion thereof. A pharmacophore model can include both the bound conformations of a ligand, or portion thereof, and one or more atoms that interact with the ligand and are from a bound polypeptide or protein. Thus, in addition to geometric characteristics of a bound conformation of a ligand, a pharmacophore model can indicate other characteristics including, for example, charge or hydrophobicity of an atom or chemical moiety. A pharmacophore model can incorporate internal interactions within the bound conformation of a ligand or interactions between a bound conformation of a ligand and a polypeptide, protein, or other receptor including, for example, van der Waals interactions, hydrogen bonds, ionic bonds, and hydrophobic interactions. A pharmacophore model can be derived from two or more bound conformations of a ligand.

As used herein, the term "ligand" refers to any compound, composition or molecule that interacts with the ligand-binding domain of a receptor and modulates its activity. A "ligand" may also include compounds that modulate the receptor without binding directly to it.

In carrying out the method of the invention, the above-described compounds may be administered as such, or in a form from which the active agent can be derived, such as a prodrug. A prodrug is a derivative of a compound described herein, the pharmacologic action of which results from the conversion by chemical or metabolic processes in vivo to the active compound. The term "prodrug esters" as employed herein includes esters and carbonates formed by reacting one or more hydroxyls of compounds used in the method of the invention with alkyl, alkoxy, or aryl substituted acylating agents employing procedures known to those skilled in the art to generate acetates, pivalates, methylcarbonates, benzoates and the like. Any compound that can be converted in vivo to provide the bioactive agent (e.g., a compound of Formula I or II) is a prodrug within the scope and spirit of the invention. Various forms of prodrugs are well known in the art. A comprehensive description of prodrugs and prodrug derivatives are described in: (a) The Practice of Medicinal Chemistry, Camille G. Wermuth et al., Ch 31 (Academic Press, 1996); (b) Design of Prodrugs, edited by H. Bundgaard (Elsevier, 1985); (c) A Textbook of Drug Design and Development, P. Krogsgaard-Larson and H. Bundgaard, eds., Ch. 5, pp. 113-191 (Harwood Academic Publishers, 1991).

The therapeutic agent used in practicing the method of the invention is generally administered in an amount sufficient to induce the desired therapeutic effect in the recipient thereof. Thus, the term "therapeutically effective amount" as used herein refers to an amount of a therapeutic agent which is sufficient to treat or prevent a condition treatable by administration of one or more of the compounds of Formula I or II or a prodrug thereof. In a particular embodiment, the therapeutically effective amount refers to the amount appropriate to treat a PCSK9-associated condition, i.e. to bring a detectable therapeutic, preventative, or ameliorative effect. The effect may include, for example, treatment or prevention of the conditions described herein.

The compound(s) described herein may be administered at a dose in range from about 0.01 mg to about 200 mg/kg of body weight per day. A dose of from 0.1 to 100 mg/kg per day, and particularly from 1 to 30 mg/kg per day in one or more applications per day or week should be effective to produce the desired result. By way of example, a suitable dose for oral administration would be in the range of 1-30 mg/kg of body weight per day, whereas a typical dose for intravenous administration would be in the range of 1-10 mg/kg of body weight per day. Of course, as those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art based on routine empirical activity testing to measure the bioactivity of the compound(s) in a bioassay, and thus establish the appropriate dosage to be administered.

The compounds used in the method of the invention will typically be administered from 1-2 times a day up to 1-2 times a week, to deliver the above-mentioned daily dosage. However, the exact regimen for administration of the compounds described herein will necessarily be dependent on the needs of the individual subject being treated, the type of treatment administered, and the judgment of the attending medical specialist.

In one aspect, the invention provides a method for treating or preventing hypercholesterolemia, and/or at least one symptom of dyslipidemia, atherosclerosis, CVD or coronary heart disease, in an individual comprising administering to the individual an effective amount of a modulator of PCSK9 function that antagonizes circulating PCSK9.

In a further aspect, the invention provides an effective amount of a modulator of PCSK9 function that antagonizes intracellular, extracellular or circulating PCSK9 for use in treating or preventing hypercholesterolemia, and/or at least one symptom of dyslipidemia, atherosclerosis, CVD or coronary heart disease, in an individual. The invention further provides the use of an effective amount of a modulator of PCSK9 function that antagonizes intracellular, extracellular or circulating PCSK9 in the manufacture of a medicament for treating or preventing hypercholesterolemia, and/or at least one symptom of dyslipidemia, atherosclerosis, CVD or coronary heart disease, in an individual.

The methods of the invention use a modulator of PCSK9 function, which refers to any molecule that blocks, suppresses or reduces (including significantly reduces) PCSK9 biological activity, including downstream pathways mediated by PCSK9 signaling, such as elicitation of a cellular response to PCSK9.

A modulator of PCSK9 function should exhibit any one or more of the following characteristics: (a) bind to PCSK9; (b) decrease or block PCSK9 interaction with the LDLR; (c) decrease or block secretion of PCSK9; (d) decrease or block PCSK9 mediated down-regulation of the LDLR; (e) inhibit the PCSK9-mediated decrease in LDL blood clearance, (f) increase LDL clearance in media by cultured hepatocytes, (g) increase blood LDL clearance by the liver in vivo, (h) improve patients' sensitivity to other LDL lowering drugs, including statins, (i) is synergistic to other LDL lowering drugs, including statins; and (j) block PCSK9 interaction with other yet to be identified factors.

In general, the compound(s) used in the method of the invention can be administered to achieve modulation of PCSK9 function by using any acceptable route known in the art, either alone or in combination with one or more other therapeutic agents. Thus, the active agent(s) can be administered orally, buccally, parenterally, such as by intravenous or intra-arterial infusion, intramuscular, intraperitoneal, intrathecal or subcutaneous injection, by liposome-mediated delivery or nanoparticle encapsulation, rectally, vaginally, by inhalation or insufflation, transdermally or by optic delivery.

The orally administered dosage unit may be in the form of tablets, caplets, pills, semisolids, soft or hard gelatin capsules, aqueous or oily solutions, emulsions, suspensions or syrups. Suitable dosage forms for parenteral administration include injectable solutions or suspensions, suppositories, powder formulations, such as nanocrystals, microcrystals or aerosol spray. The active agent may also be incorporated into a conventional transdermal delivery system.

As used herein, the expression "physiologically compatible carrier medium" includes any and all solvents, diluents, or other liquid vehicle, dispersion or suspension aids, surface agents, isotonic agents, thickening or emulsifying agents, preservatives, solid binders, lubricants, fillers and the like as suited for the particular dosage form desired. Remington: The Science and Practice of Pharmacy, $20^{th}$ edition (A. R. Genaro et al., Part 5, Pharmaceutical Manufacturing, pp. 669-1015 (Lippincott Williams & Wilkins, Baltimore, MD/Philadelphia, PA) (2000)) discloses various carriers used in formulating pharmaceutical compositions and known techniques for the preparation thereof. Except insofar as any conventional pharmaceutical carrier medium is incompatible with the PCSK9 modulators used in the present invention, such as by producing an undesirable biological effect or otherwise interacting in a deleterious manner with any other component(s) of a formulation comprising such compounds, its use is contemplated to be within the scope of this invention.

For the production of solid dosage forms, including hard and soft capsules, the therapeutic agent may be mixed with pharmaceutically inert, inorganic or organic excipients, such as lactose, sucrose, glucose, gelatin, malt, mannitol, silica gel, starch or derivatives thereof, talc, stearic acid or its salts, dried skim milk, vegetable, petroleum, animal or synthetic oils, wax, fat, polyols, and the like. For the production of liquid solutions, emulsions or suspensions or syrups one may use excipients such as water, alcohols, aqueous saline, aqueous dextrose, polyols, glycerin, lipids, phospholipids, cyclodextrins, vegetable, petroleum, animal or synthetic oils. For suppositories, one may use excipients, such as vegetable, petroleum, animal or synthetic oils, wax, fat and polyols. For aerosol formulations, one may use compressed gases suitable for this purpose, such as oxygen, nitrogen and carbon dioxide. The pharmaceutical composition or formulation may also contain one or more additives including, without limitation, preservatives, stabilizers, e.g., UV stabilizers, emulsifiers, sweeteners, salts to adjust the osmotic pressure, buffers, coating materials and antioxidants.

The present invention further includes controlled-release, sustained-release, or extended-release therapeutic dosage forms for administration of the active agent, which involves incorporation of the active agent into a suitable delivery system. This dosage form controls release of the active agent(s) in such a manner that an effective concentration of the active agent(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the active agent.

Compounds for use in practicing this invention include PCSK9 antagonists such as those of Formula I and particularly Formula II, above. In a particular embodiment, the PCSK9 antagonist is selected from the group consisting of SBC-115,418, SBC-115,433, SBC-115,448, SBC-115,462 and SBC-115,477 (see, e.g., FIG. 3). In a particular embodiment, the PCSK9 antagonist is SBC-115,418.

The methods of the present invention will normally include medical follow-up to determine the therapeutic or prophylactic effect brought about in the subject undergoing treatment with the compound(s) and/or composition(s) described herein.

Definitions

The following definitions are provided to facilitate an understanding of the present invention:

The singular forms "a," "an," and "the" include plural referents unless the context clearly dictates otherwise.

As used herein, the term "alkyl" is a branched or unbranched saturated hydrocarbon chain moiety. "Lower alkyl" denotes branched or unbranched hydrocarbon chains, having 1 to about 8 carbons, such as, methyl, ethyl, n-propyl, iso-propyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group which may be substituted with one or more substituent groups which are attached commonly to such chains, such as, hydroxy, halogen, mercapto or thio, cyano, alkylthio, carboxy, carbalkoxy, amino, nitro, alkoxy, or optionally substituted, alkenyl, alkynyl, heterocyclyl, aryl, heteroaryl, and the like to form alkyl groups such as trifluoro methyl, 3-hydroxyhexyl, 2-carboxypropyl, 2-fluoroethyl, carboxymethyl, cyanobutyl, phenethyl, benzyl and the like.

The term "halogen" or "halo" as used herein alone or as part of another group refers to chlorine, bromine, fluorine, and iodine.

The term "alkoxy" refers to alkyl-O—, in which alkyl is as defined above.

Unless otherwise indicated, the term "cycloalkyl" as employed herein alone or as part of another group includes saturated or partially unsaturated (containing 1 or more double bonds) cyclic hydrocarbon groups ('carbocycle') containing 1 to 3 rings, including monocyclic alkyl, bicyclic alkyl and tricyclic alkyl, containing a total of 3 to 20 carbons forming the rings, particularly 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl, cyclododecyl and cyclohexenyl.

"Substituted cycloalkyl" includes a cycloalkyl group which may be substituted with 1 or more substituents such as halogen, alkyl, substituted alkyl, alkoxy, hydroxy, aryl, substituted aryl, aryloxy, cycloalkyl, alkylamido, alkanoylamino, oxo, acyl, arylcarbonylamino, amino, nitro, cyano, thiol and/or alkylthio and/or any of the substituents included in the definition of "substituted alkyl."

Unless otherwise indicated, the term "aryl" or "Ar" as employed herein alone or as part of another group refers to monocyclic and polycyclic aromatic groups containing 6 to 10 carbons in the ring portion (such as phenyl or naphthyl including 1-naphthyl and 2-naphthyl) and may optionally include one to three additional rings fused to a carbocyclic ring, such as a cycloalkyl ring or fused to an aryl or heterocyclic ring or substituted forms thereof.

"Substituted aryl" includes an aryl group which may be substituted with one or more substituent groups, such as halo, alkyl, haloalkyl (e.g., trifluoromethyl), alkoxy, haloalkoxy (e.g., difluoromethoxy), alkenyl, alkynyl, cycloalkyl-alkyl, heterocyclo-alkyl, aryl, heteroaryl, arylalkyl, aryloxy, aryloxyalkyl, arylalkoxy, alkoxycarbonyl, alkylcarbonyl, arylcarbonyl, arylalkenyl, aminocarbonyl, monoalkylaminocarbonyl, dialkylaminocarbonyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are optionally substituted alkyl, aryl or any of the other substituents mentioned in the definitions), thiol, alkylthio, heteroarylthio, arylthioalkyl, alkoxyarylthio, alkylaminocarbonyl, arylaminocarbonyl, alkylcarbonyloxy, arylcarbonyloxy, alkylcarbonylamino, arylcarbonylamino, arylsulfinylalkyl, arylsulfonylamino or arylsulfonaminocarbonyl and/or any of the alkyl substituents referred to above.

Unless otherwise indicated, the term "heteroaryl" or "Het" as used herein alone or as part of another group refers to a 5- or 7-membered aromatic ring which includes 1, 2, 3 or 4 hetero atoms such as nitrogen, oxygen or sulfur and such rings fused to an aryl, cycloalkyl, heteroaryl or heterocycloalkyl ring and includes possible N-oxides. Examples of heteroaryl groups include pyrrolyl, furanyl, thienyl, pyrazolyl, imidazolyl, pyridyl, pyrazinyl, pyrimidinyl, pyridazinyl, oxazolyl, isooxazolyl, thiazolyl, isothiazolyl, thiadiazolyl and oxadiazolyl. Examples of fused heteroaryl groups include quinoline, isoquinoline, indole, isoindole, carbazole, acridine, benzimidazole, benzofuran, benzoxazole, isobenzofuran, benzothiophene, phenanthroline, purine, and the like. "Substituted heteroaryl" includes a heteroaryl group, which may be substituted with 1 to 4 substituents, such as the substituents included above in the definition of "substituted alkyl," "substituted cycloalkyl," and "substituted aryl."

The term "heterocyclo", "heterocycle" or "heterocyclic ring," as used herein alone or as part of another group, represents an unsubstituted or substituted stable 5- to 7-membered monocyclic ring system which may be saturated or partially unsaturated, and which consists of carbon atoms and from one to four heteroatoms selected from N, O, or S, and wherein the nitrogen and sulfur heteroatoms may optionally be oxidized, and the nitrogen heteroatom may optionally be quaternized. "Substituted heterocyclo" (or heterocycle or heterocyclic ring) includes a heterocyclic group which may be substituted with 1 to 4 substituents, such as the substituents included above in the definition of "substituted alkyl," "substituted cycloalkyl," and "substituted aryl." The heterocyclic ring may be attached at any heteroatom or carbon atom, which results in the creation of a stable structure. Examples of such heterocyclic groups include, but are not limited to, piperidinyl, piperazinyl, oxopiperazinyl, oxopiperidinyl, oxopyrrolidinyl, oxoazepinyl, azepinyl, pyrrolidinyl, pyrazolidinyl, imidazolinyl, oxazolidinyl, isoxazolidinyl, morpholinyl, thiazolidinyl, tetrahydropyranyl, thiamorpholinyl, thiamorpholinyl sulfoxide and thiamorpholinyl sulfone.

The term "optionally substituted" is used herein to signify that a chemical moiety referred to, e.g., alkyl, aryl, heteroaryl, may be unsubstituted or substituted with one or more groups including, without limitation, lower alkyl, alkenyl, alkynyl, cycloalkyl, arylalkyl, aryl, haloaryl, heterocycle, heterocycloalkyl, heteroaryl, hydroxyl, amino, monoalkylamino, dialkylamino, alkoxy, halogen, haloalkoxy, aryloxy, aryloxyalkyl, alkylaryloxy, arylalkoxy, alkoxyaryl, carboxy, carbalkoxy, carboxamido, aminocarbonyl, monoalkylaminocarbonyl, dialkylaminocarbonyl, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinylalkyl and the like. The chemical moieties of formulas I and II, above, that may be optionally substituted include lower alkyl, alkenyl, alkynyl, cycloalkyl, arylalkyl, aryl, heterocycle, and heteroaryl. For example, optionally substituted alkyl would comprise both propyl and 2-chloro-propyl. Additionally, "optionally substituted" is also inclusive of embodiments where the named substituent or substituents have multiple substituents rather than simply a single substituent. For example, optionally substituted aryl would comprise both phenyl and 3-bromo-4-chloro-6-ethyl-phenyl.

Unless expressly indicated otherwise, all references herein to alkyl and aryl groups also include the substituted forms thereof.

The activities of compounds described herein have been experimentally demonstrated. The following examples are provided to describe the invention in further detail. These examples are provided for illustrative purposes only and are not intended to limit the invention in any way.

Example 1

In Vitro Test for LDLR/PCSK9 Binding

Testing of SBC-115,418 and analogs was performed in a binding assay to determine their ability to inhibit the PCSK9/LDLR interaction. SBC-115,418 inhibited the PCSK9/LDLR interaction with an $IC_{50}$ in the sub-micromolar range. Experimental details are provided hereinabove and in WO 2017/222953. Several new analogs (see FIG. 3) also inhibited in the sub-micro-molar (SBC-115,433 and SBC-115,477) or low micro-molar (SBC-115,448 and SBC-115,462) range (FIG. 4A). Given the lipophilicity of lead compound SBC-115,418, a solubility study was undertaken to look at its effects on binding (FIG. 4B). An in vitro ELISA binding assay was performed at different concentrations (0.01 μM-100 μM) of SBC-115,418 under different solubilization conditions. The data showed that in vitro binding of SBC-115,418 using improved solubility conditions resulted in a significant improvement in the binding potency, with an $IC_{50}$ of 50 nM. In addition, increased potency was further observed by formal replacement of the oxygen atom of the benzoxazole moiety of SBC-115,418 by a nitrogen atom to make a benzimidzole moiety (SBC-115,477; log P=4.5), resulting in increased solubility and an $IC_{50}$ of 0.19 μM.

Example 2

Test for Secreted PCSK9

SBC-115,418 and its analogs exhibited no effect on the synthesis, processing and secretion of PCSK9 either in the cells or into the media. Experimental details are provided hereinabove and in WO 2017/222953.

Example 3

Cell-Based Assay for LDLR Upregulation and Uptake of DiI-LDL In Situ

SBC-115,418, SBC-115,433, SBC-115,448 and SBC-115,462 exhibited an increase in the level of LDLR as compared to cells treated with the same volume of DMSO (control) with a significant upregulation of LDLR. In addition, SBC-115,418 and SBC-115,462 exhibited significant increase in the DiI-LDL uptake in HepG2 cells at 10 μM concentrations (FIG. 5).

Example 4

Optimization Process of SBC-115,418 Nanoformulations

Several SBC-115,418 Nanoformulations were prepared and optimized (FIG. 1A-1D). Constituents and their amounts for SBC Nanoformulations no.'s 1-3 are provided in Tables 1 and 2. SBC-115,418, PVP (average Molecular Weight 40,000), HPMC-AS and Alginic acid in DMSO were added to water under probe sonication for 1-2 minutes at room temperature. Then the above solutions were incubated for 30 minutes at room temperature. The NP suspensions were washed twice with water using centrifugation (15,000× g, 4° C., 60 minutes). Alginic acid was replaced with Lactobionic acid or, for Formulation no. 4, with Glycyrrhetinic acid (GA).

TABLE 1

Optimization of Process Parameters for the Production of Nano Crystals with Methylcellulose Derivative and Polyvinyl Pyrrolidone Coated Lactobionic Acid. PVP, polyvinyl pyrrolidone; HPMCAS, hydroxypropyl methylcellulose acetate succinate.

| Nanoformulation Code # | SBC-115,418 (mg) | PVP 40K (mg) | HPMCAS-MMP (mg) | Lactobionic acid (LA) (mg) |
|---|---|---|---|---|
| No. 1 | 20 | 20 | 20 | 1 |
| No. 2 | 21 | 10 | 20 | 1 |
| No. 3 | 22 | 10 | 10 | 1 |

Table 2 illustrates the size, zeta potentials and Entrapment Efficiency (%) of optimized Nanoformulations no.'s 1-3. Table 2 further includes no. 3 where 5% mannitol was added as cryoprotectant to prevent aggregation. Nanoformulation no. 3 was desirable because of its smaller size.

TABLE 2

Entrapment Efficiency (%). HPLC-UV used to quantify SBC-115,418 in NPs.

| Nanoformulation Code # | Size (nm) | PDI | Zeta Potential (mv) | EE (%) |
|---|---|---|---|---|
| No. 1 | 162 | 0.17 | −19 | 86 |
| No. 2 | 208 | 0.19 | −17 | 95 |
| No. 3 | 116 | 0.16 | −11.9 | 95 |
| No. 3 after 5% Mannitol | 128 | 0.15 | −30.9 | 95 |

Example 5

PK and PD Analysis of Nanoformulations of SBC-115,418

SBC-115,418/Nanoformulation D (SBC-115,418, PVP, Alginic acid, Chitosan oligosaccharide lactate) was used to determine PK and PD. For PK and oral bioavailability of SBC-115,418, the data showed increased concentrations of SBC-115,418 (5 mg/kg oral and i.p.) observed from 30 min to 1 hour in mice plasma. The data shows that SBC-115,418 has 18% oral bioavailability (FIG. 6). For PD, the effect of SBC-115,418 on LDL cholesterol levels in high-fat diet (HFD) fed C57/Black6 mice showed a 20% LDL-C reduction after the administration of SBC-115,418 for 5 days (FIG. 7).

Example 6

Analysis of SBC-115,418 Dispersion and Hepatic Targeted Formulations

HPMC-AS is a widely used excipient that possesses increased solubility, capable of forming a solid dispersion and inhibiting the crystallization of the API from the dispersion matrix as well as a rate-controlling polymer for sustained-release dose form. The dispersions were prepared as follows: SBC-115,418 was solubilized in HPMC-AS using sonication for 10 minutes. Using SBC-115,418/HPMC-AS as a Dispersion formulation versus the Nanocrystal/Hepatic Targeting optimal formulation, Nano SBC-115,418 (SBC-115,418/PVP/HPMC-AC/Alginic Acid) (FIG. 2), the Dispersion formulation showed a greater AUC, $C_{max}$ in blood, and oral bioavailability % F for SBC-115,418 in mice (Table 3). However, greater hepatic delivery of SBC-115,418 was obtained with Nano SBC-115,418 versus the Dispersion formulation of SBC-115,418 (FIGS. 8 and 9). Furthermore, the effect of Nano SBC-115,418 on LDL-C levels in C57BL/6 mice fed high-fat diet shows unexpectedly greater LDL-C efficacy with Nano SBC-115,418 versus the Dispersion formulation of SBC-115,418 (FIG. 10).

TABLE 3

Pharmacokinetics of Nano SBC-115,418 versus SBC-115,418 solubilized in HPMC-AS (Dispersion) are provided including the measured PK parameters (AUC, Cmax, Tmax) and calculated oral bioavailability (% F) of both subcutaneous (SC) and oral administration of the optimized Nanocrystal/Hepatic Targeting Formulation (Nano SBC-115,418) versus an HPMC-AS dispersion (SC and oral) of SBC-115,418.

| SBC-115,418 Formulation | AUC (ng h/mL) | Cmax (ng/mL) | Tmax (h) | Oral Bioavailability % F |
|---|---|---|---|---|
| Nanocrystal/Hepatic Targeting (SC) Nano SBC-115,418 | 339.5 | 40 | 4 | 100 |
| Nanocrystal/Hepatic Targeting (Oral) Nano SBC-115,418 | 773 | 20 | 12 | 22.7 |
| HPMC-AS Dispersion (SC) | 356.7 | 57 | 2 | 100 |
| HPMC-AS Dispersion (Oral) | 1810 | 154 | 0.25 | 50.7 |

Example 7

Test with Nutritionally-Induced Hypercholesterolemia Mouse Model

Mice were housed as four animals per cage under climate-controlled conditions of temperature (20-24° C.), humidity (60-70%), and alternating 12 hour light/dark cycles. Mice were fed a high-fat diet (TD.06414, Harlan Research Diet, Inc., Indianapolis, Ind.) that provides 60 calories from fat sources to increase total cholesterol. The nutritionally induced mouse is therefore a suitable model for examining the effects of Nano SBC-115,418 for liver targeting in lowering LDL-C levels. Male C57BL/6 mice were fed either a commercial chow diet (Prolab RMH 3000, PMI feeds, St. Louis, Mo.) to serve as a negative control, or a high-fat diet (TD.06414, Harlan Research Diet, Inc., Indianapolis, Ind.). Plasma was collected once weekly to monitor the level of LDL-C and PCSK9 levels. After 4 weeks of feeding on the high-fat diet, mice were randomly assigned to one of the different groups such that the average of each biomarker level are comparable among the different groups. One group was treated with vehicle, and the other groups are treated with Nano SBC-115,418 at different doses (Table 4). Blood samples (75 µl) were collected from the retro-orbital venous plexus via heparinized capillary tubes containing 2 USP units of ammonium heparin per tube (Carolina, Burlington, NC). Plasma was separated immediately by centrifugation (5,000×g) for 5 minutes at room temperature and then kept at −80° C. until assayed for lipid profile. Plasma total and free cholesterol, LDL-C and free PCSK9 levels were measured.

TABLE 4

Dose and Route of Administration of Nano SBC-115,418 in High-Fat Fed Mice. The treatment schedule for the pharmacodynamics effects of Nano SBC-115,418 on Lipid Profiles in mice fed a high-fat diet are provided. N = Number of mice per study cohort. Blood collected after 24 hours of treatment, 1 week, and 2 weeks.

| | N | |
|---|---|---|
| PBS (0 mg/kg) | | oral administration |
| 1 mg/kg | 6 | oral administration |
| 3 mg/kg | 6 | oral administration |
| 10 mg/kg | 6 | oral administration |
| 30 mg/kg | 6 | oral administration |
| 3 mg/kg | 6 | subcutaneous |

The data demonstrates that Nano SBC-115,418 is highly effective at lowering LDL-C and PCSK9 in mice fed high-fat diet (FIGS. 11-16). In addition, Nano SBC-115,418 causes a significant increase (2-fold) in HDL cholesterol. Oral administration (30 mg/kg) of Nano SBC-115,418 alone in mice fed high-fat diet resulted in close to 90% LDL-C lowering and is more potent than the monoclonal antibody. In addition, Nano SBC-115,418 causes a concentration dependent increase in the levels of LDL-receptor in the liver (FIG. 17). In view of the foregoing, Nano SBC-115,418 clearly demonstrates unexpectedly superior properties for reducing LDL-C.

The specification includes citations to certain publications, which are provided to indicate the state of the art to which this invention pertains. The entire disclosure of each of the cited publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified but is capable of considerable variation and modification without departure from the scope of the appended claims. Furthermore, the transitional terms "comprising," "consisting essentially of," and "consisting of," when used in the appended claims, in original and amended form, define the claim scope with respect to what un-recited additional claim elements or steps, if any, are excluded from the scope of the claim(s). The term "comprising" is intended to be inclusive or open-ended and does not exclude any additional, un-recited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed invention. All compositions and methods of use thereof that embody the present invention can, in alternate embodiments, be more specifically defined by any of the transitional terms "comprising," "consisting essentially of," and "consisting of."

REFERENCES

1. Grundy et al. (2004) *Circulation* 110, 227-239.
2. Abifadel et al. (2003) *Nature Genetics* 34, 154-156.
3. Pisciotta et al. (2006) *Atherosclerosis* 186, 433-440.
4. Maxwell and Breslow (2004) *Proc Natl Acad Sci USA* 101, 7100-7105.
5. Benjannet et al. (2004) *J Biol Chem* 279, 48865-48875.
6. Cohen et al. (2005) *Nature Genetics* 37, 161-165.
7. Rashid et al. (2005) *Proc Natl Acad Sci USA* 102, 5374-5379.
8. Zhao et al. (2006) *Am J Human Genetics* 79, 514-523.
9. Benjannet et al. (2006) *J Biol Chem* 281, 30561-30572.
10. Li et al. (2007) *Biochem J* 406, 203-207.
11. McNutt et al. (2007) *J Biol Chem* 282, 20799-20803.
12. Zhang et al. (2007) *J Biol Chem* 282, 18602-18612.
13. Kwon et al. (2008) *Proc Natl Acad Sci USA* 105, 1820-5.
14. Bottomley et al. (2009) *J Biol Chem* 284, 1313-1323.
15. Seidah N G (2009) *Expert Opin Ther Targets* 13, 19-28.
16. Graham et al. (2007) *J Lipid Res* 48, 763-767.
17. Frank-Kamenetsky et al. (2008) *Proc Natl Acad Sci USA* 105, 11915-11920.
18. Piper et al. (2007) *Structure* 15, 545-552.
19. Cunningham et al. (2007) *Nature Struc Mol Biol* 14, 413-419.
20. Seidah et al. (2003) *Proc Natl Acad Sci USA* 100, 928-933.
21. McNutt et al. (2009) *J Biol Chem* 284, 10561-10570.
22. Swergold et al. (2010) *Circulation* 122, A23251.
23. Dias et al. (2011) *Circulation* 124.
24. Amgen (2010) Ascending Multiple Dose Study to Evaluate the Safety, Tolerability, Pharmacokinetics and Pharmacodynamics of AMG 145 in Subjects with Hyperlipidemia on Stable Doses of a Statin. ClinicalTrails.Gov.

What is claimed:

1. A nanoparticle comprising at least one PCSK9 antagonist encapsulated within the nanoparticle, wherein said PCSK9 antagonist is a compound of Formula (I):

(I)

including pharmaceutically acceptable salts and stereoisomers of said compound, wherein $R_1$ is H or $CH_3$; $R_2$ and $R_3$ are independently selected from the group consisting of H, halogen, $(C_1-C_3)$-alkyl and $(C_1-C_3)$-alkoxy; and $R_4$ is selected from the group consisting of $CO_2R_5$, $CONR_5R_6$, aryl, and heteroaryl, wherein $R_5$ and $R_6$ are independently selected from the group consisting of H and $(C_1-C_3)$-alkyl, wherein said aryl and heteroaryl are independently substituted or unsubstituted, wherein said nanoparticle comprises polyvinyl pyrrolidone (PVP) and hydroxypropyl methylcellulose acetate succinate (HPMC-AS), and wherein said nanoparticle comprises a liver targeting moiety on the exterior of the nanoparticle.

2. The nanoparticle of claim 1, wherein $R_4$ is an aryl or heteroaryl.

3. The nanoparticle of claim 2, wherein $R_4$ is selected from the group consisting of 2-oxazole, 2-oxazoline, 2-benzoxazole and 2-benzimidazole.

4. The nanoparticle of claim 1, wherein said PCSK9 antagonist is a compound of Formula (II):

(II)

including pharmaceutically acceptable salts and stereoisomers of said compounds, wherein $R_1$ is H or $CH_3$; $R_2$ is H or methoxy; $R_3$ is H or halogen; and $R_7$ is independently selected from the group consisting of H and $(C_1-C_2)$-alkyl or $R_7$ are taken together to form an optionally substituted 6-membered carbocycle.

5. The nanoparticle of claim 4, wherein when $R_1$ is H, then $R_2$ is H, and when $R_1$ is methyl then $R_2$ is methoxy.

6. The nanoparticle of claim 4, wherein $R_7$ are taken together to form an aryl.

7. The nanoparticle of claim 1, wherein said halogen is fluorine.

8. The nanoparticle of claim 1, wherein said PCSK9 antagonist is selected from the group consisting of (SBC-115, 418)

-continued (SBC-115, 433)
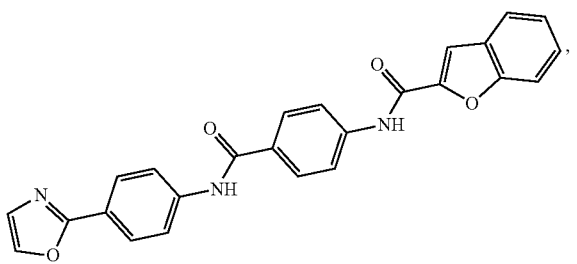

(SBC-115, 448)
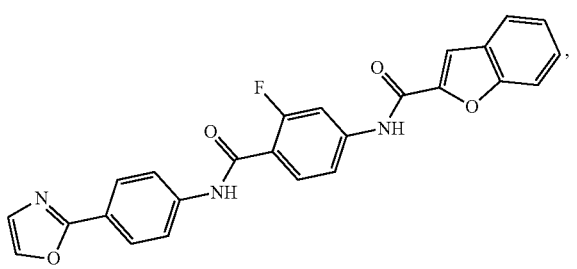

(SBC-115, 462)
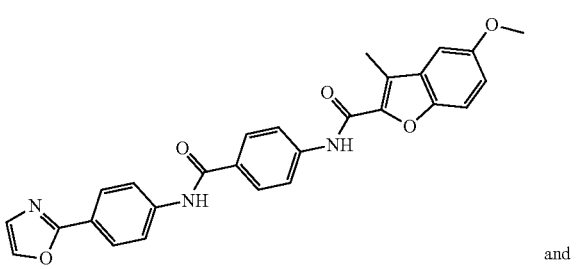

and (SBC-115, 477)
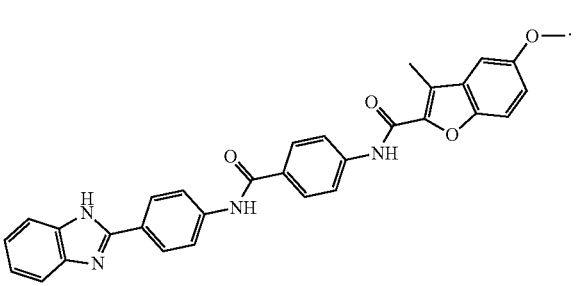

9. The nanoparticle of claim 1, wherein said PCSK9 antagonist is (SBC-115, 418)
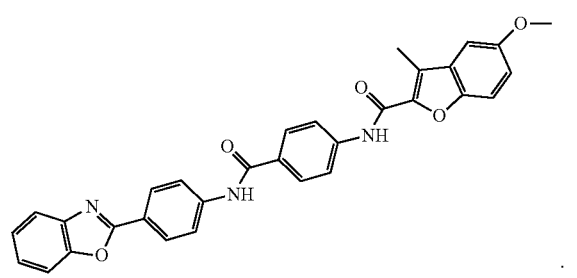

10. The nanoparticle of claim 1, wherein said nanoparticles are hydrophobic.

11. The nanoparticle of claim 1, wherein said liver targeting moiety is selected from the group consisting of glycyrrhetinic acid (GA), lactobionic acid (LA), alginic acid and combinations thereof.

12. The nanoparticle of claim 1, wherein said nanoparticle further encapsulates at least one other LDL-lowering substance.

13. The nanoparticle of claim 12, wherein said LDL-lowering substance is an anti-dyslipidemia agent.

14. The nanoparticle of claim 13, wherein said anti-dyslipidemia agent is a statin, ezetimibe, bempedoic acid, a thyroid hormone receptor beta agonist, or a combination thereof.

15. A composition comprising a nanoparticle of claim 1 and a physiologically compatible carrier medium.

16. A method for delivering a PCSK9 antagonist to the liver of a subject, said method comprising administering at least one nanoparticle claim 1 to said subject.

17. The method of claim 16, wherein said subject is human.

18. The methods of claim 16, wherein said nanoparticle is administered to said subject in a composition further comprising a physiologically compatible carrier medium.

19. A method for lowering low-density lipoprotein cholesterol (LDL-C), in a subject, said method comprising administering at least one nanoparticle of claim 1 to said subject.

20. The method of claim 19, wherein said subject is human.

21. The methods of claim 19, wherein said nanoparticle is administered to said subject in a composition further comprising a physiologically compatible carrier medium.

22. The method of claim 19, wherein said subject has hypercholesterolemia.

23. A method for treating hypercholesterolemia, in a patient in need of said treatment, the method comprising administering to said patient a therapeutically effective amount of at least one nanoparticle of claim 1.

24. The methods of claim 23, wherein said nanoparticle is administered to said subject in a composition further comprising a physiologically compatible carrier medium.

25. The method of claim 16, further comprising the administration of at least one other LDL-lowering substance.

26. The method of claim 25, wherein said LDL-lowering substance is an anti-dyslipidemia agent.

27. The method of claim 26, wherein said anti-dyslipidemia agent is a statin, ezetimibe, bempedoic acid, a thyroid hormone receptor beta agonist, or a combination thereof.

28. A compound selected from the group consisting of
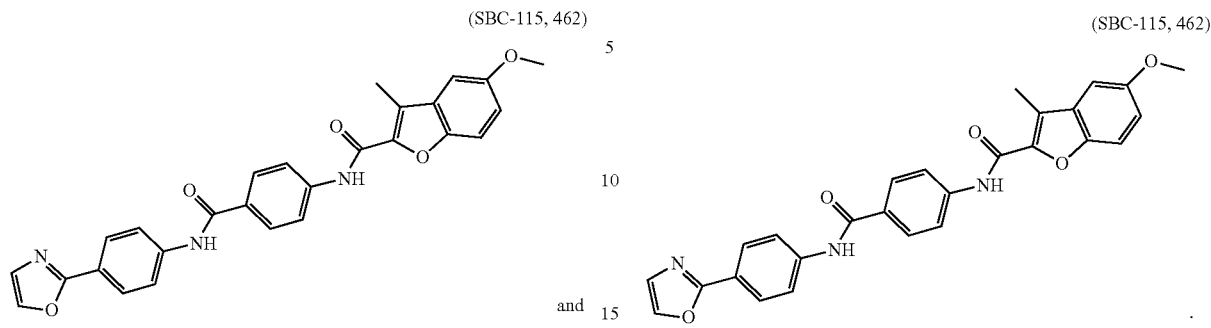
and
29. The compound of claim 28 which is
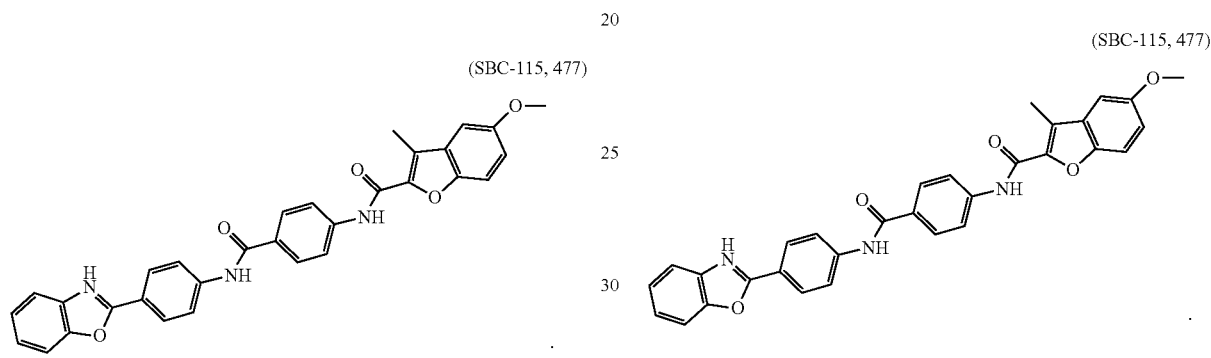
30. The compound of claim 28 which is
* * * * *